US008436177B2

(12) United States Patent
Stowasser et al.

(10) Patent No.: US 8,436,177 B2
(45) Date of Patent: *May 7, 2013

(54) SALTS AND CRYSTALL FORMS OF 2-METHYL-2-[4-(3-METHYL-2-OXO-8-QUINOLIN-3-YL-2,3-DIHYDRO-IMIDAZO[4,5-C]QUINOLIN-1-YL)-PHENYL]-PROPIONITRILE

(75) Inventors: Frank Stowasser, Murg (DE); Markus Bänziger, Bubendorf (CH); Sudhakar Devidasrao Garad, Malden, MA (US)

(73) Assignee: Novartis AG, Basel (CH)

( * ) Notice: Subject to any disclaimer, the term of this patent is extended or adjusted under 35 U.S.C. 154(b) by 660 days.

This patent is subject to a terminal disclaimer.

(21) Appl. No.: 12/514,976

(22) PCT Filed: Nov. 16, 2007

(86) PCT No.: PCT/US2007/084893
§ 371 (c)(1),
(2), (4) Date: Mar. 16, 2010

(87) PCT Pub. No.: WO2008/064093
PCT Pub. Date: May 29, 2008

(65) Prior Publication Data
US 2010/0168153 A1 Jul. 1, 2010

Related U.S. Application Data

(60) Provisional application No. 60/866,483, filed on Nov. 20, 2006.

(51) Int. Cl.
*C07D 471/06* (2006.01)
*C07D 471/16* (2006.01)
*A61K 31/437* (2006.01)

(52) U.S. Cl.
USPC .......................................... 546/82; 514/293

(58) Field of Classification Search .............. 546/82; 514/293
See application file for complete search history.

(56) References Cited

U.S. PATENT DOCUMENTS

| 4,929,624 | A | 5/1990 | Gerster |
| 5,525,612 | A | 6/1996 | Gerster |
| 7,667,039 | B2 | 2/2010 | Garcia-Echeverria |
| 2008/0194579 | A1 | 8/2008 | Garcia-Echeverria |
| 2010/0056558 | A1 | 3/2010 | Garcia-Echeverria |

FOREIGN PATENT DOCUMENTS

| CL | 1187-2006 | 9/2006 |
| EP | 1104764 | 6/2001 |
| WO | 03/097641 | 11/2003 |
| WO | 2005/054237 | 6/2005 |
| WO | 2005/054238 | 6/2005 |
| WO | 2006/122806 | 11/2006 |

OTHER PUBLICATIONS

Berge S. et al. Pharmaceutical Salts, 1977.*
Vippagunta S.R. et al: "Crystalline solids", Advanced Drug Delivery Reviews (2001) vol. 48, pp. 3-26.
Maira Sauveur-Michel, et al: "Class IA phosphatidylinositol 3-kinase: from their biologic implication in human cancers to drug discovery", Expert Opinion Ther. Targets (2008), vol. 12(2) pp. 223-238.
Thomas Matt et al: "Inhibition of PI-3 kinase for treating respiratory disease: good idea or bad idea?", ScienceDirect, (2008) vol. 8, pp. 267-274.
Crabbe Tom et al: "The PI3K inhibitor arsenal: choose your weapon!", Trends in Biochemical Sciences, (2007) vol. 32, No. 10, pp. 450-456.
Cancer Drug Design and Discovery, Neidle, Stephen ed. (Elsevier/Academic Press, 2008), pp. 427-431.
Diario Oficial de la Republica de Chile, No. 38.566, dated Sep. 15, 2006, item No. 1187-06.
Bastin et al: "Salt selection and optimisation procedures for pharmaceutical new chemical entities", Organic Process Research & Development 2000, 4(5):427-435 Jul. 19, 2000.
Caira, Mino R.: "Crystalline polymorphism of Organic Compounds", Topics in Current chemistry, vol. 198, Springer Verlag Berlin Heidelberg 1998, pp. 163-208.
Byrn, Stephen, et al: "Pharmaceutical solids: a strategic approach to regulatory considerations", Pharmaceutical Research, Kluwer Academic Publishers, New York, NY, vol. 12, No. 7, Jul. 1, 1995, pp. 945-954.
Guillory J K Ed—Brittain H G: "Generation of polymorphs, hydrates, solvates, and amorphous solids", Polymorphism in Pharmaceutical Solids, Jan. 1, 1999, pp. 183-226.
Harwood L M et al: "Experimental organic chemistry—Principles and practice", Jan. 1, 1989, Experimental Chemistry—Organic Chemistry and Reaction, pp. 127-132.
Anderson et al: "Tools for purifying the product: column chromatography, crystallization and reslurrying", Practical Process Research and Development, Academic Press, San Diego, US, Jan. 1, 2000, pp. 223-247.
Maira, Sauveur-Michel et al: "Identification and characterization of NVP-BEZ235, a new orally available dual phosphatidylinositol 3-kinase/mammalian target of rapamycin inhibitor with potent in vivo antitumor activity", Molecular Cancer Therapeutics 2008; 7(7), Jul. 2008, pp. 1851-1863.
Bernstein J Ed et al: "Conventions for naming polymorphs", Jan. 1, 2002, Polymorphism in Molecular Cyrstals; [Iucr Monographs on Crsyatllography; 14], Claredon Press, Oxford, GB, p. 8.
"Polymorphism in pharmaceutical solids ED—Brittain H G", Polymorphis in Pharmaceutical Solids, No. 1/02 Jan. 1, 1999, pp. 141-161, 184/1.
Akira Suzuki. "Recent advances in the cross-coupling reactions of organoboron derivatives with organic electrophiles, 1995-1998." Journal of Organometallic Chemistry, vol. 576, Issues 1-2, Mar. 15, 1999, pp. 147-168.

* cited by examiner

*Primary Examiner* — Rita Desai
(74) *Attorney, Agent, or Firm* — Sandra Rueck

(57) ABSTRACT

The invention relates to particular crystalline forms of 2-methyl-2-[4-(3-methyl-2-oxo-8-quinolin-3-yl-2,3-dihydro-imidazo[4,5-c]quinolin-1-yl)-phenyl]-propionitrile, its hydrates and solvates, its salts and hydrates and solvates of its salts, certain processes for their preparation, pharmaceutical compositions containing these crystalline forms, and their use in diagnostic methods or, preferably, for the therapeutic treatment of warm-blooded animals, especially humans, and their use as an intermediate or for the preparation of pharmaceutical preparations for use in diagnostic methods or, preferably, for the therapeutic treatment of warm-blooded animals, especially humans.

32 Claims, 17 Drawing Sheets

FIG. 1  Form A of 2-methyl-2-[4-(3-methyl-2-oxo-8-quinolin-3-yl-2,3-dihydro-imidazo[4,5-c]quinolin-1-yl)-phenyl]-propionitrile
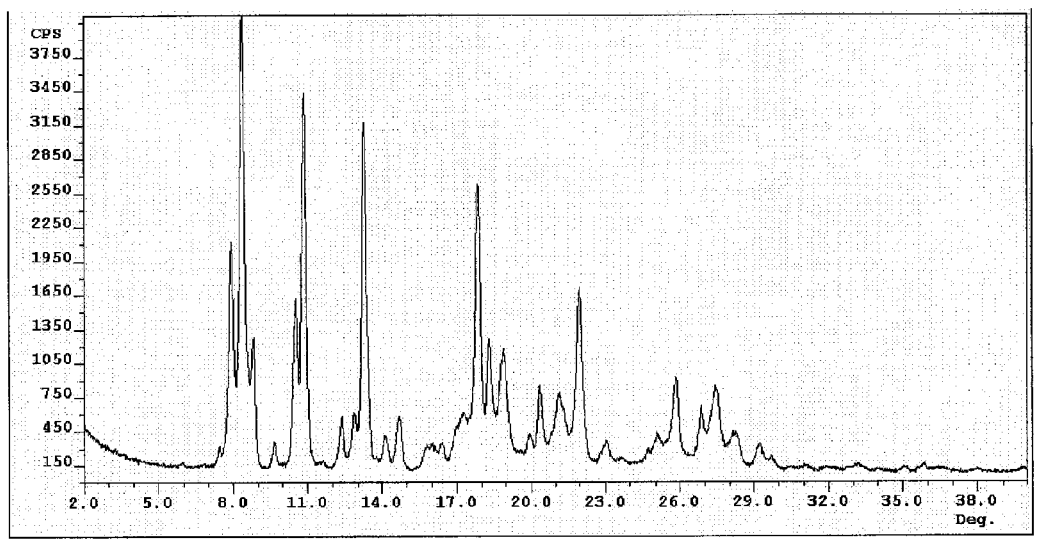

FIG. 2 Form B of 2-methyl-2-[4-(3-methyl-2-oxo-8-quinolin-3-yl-2,3-dihydro-imidazo[4,5-c]quinolin-1-yl)-phenyl]-propionitrile
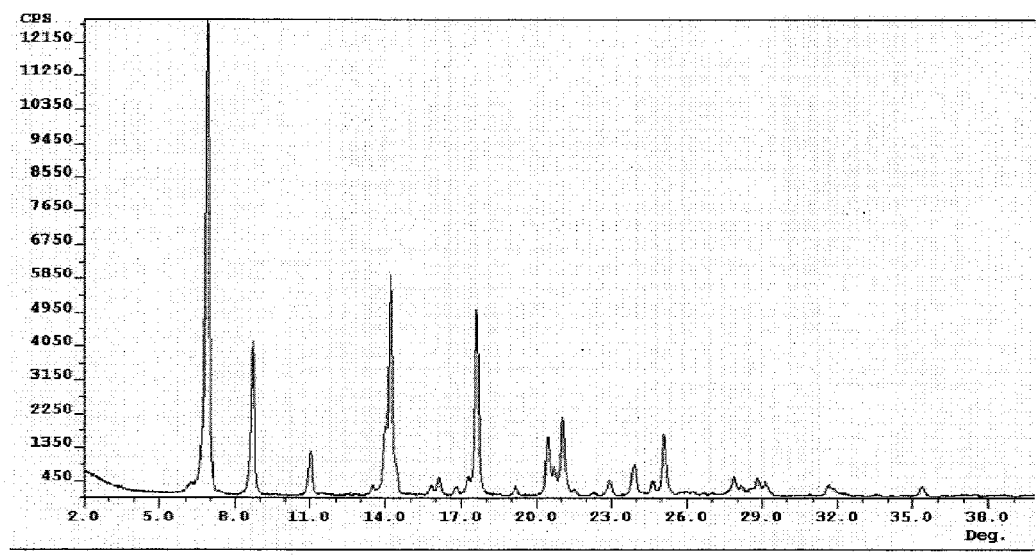

FIG. 3 Form C of 2-methyl-2-[4-(3-methyl-2-oxo-8-quinolin-3-yl-2,3-dihydro-imidazo[4,5-c]quinolin-1-yl)-phenyl]-propionitrile
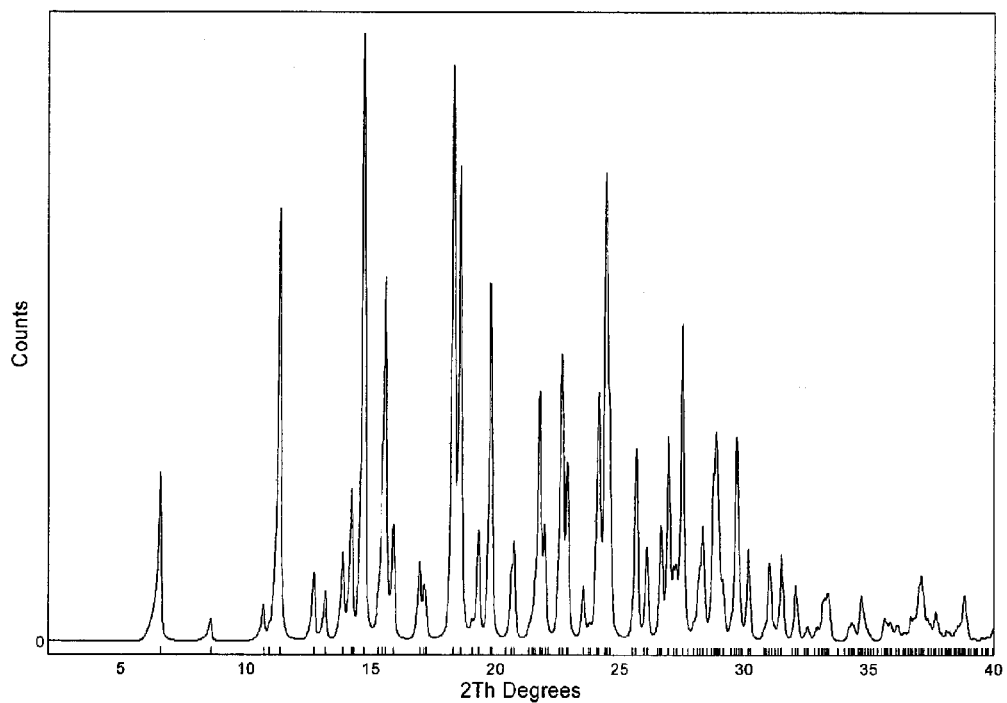

FIG. 4   Form D of 2-methyl-2-[4-(3-methyl-2-oxo-8-quinolin-3-yl-2,3-dihydro-imidazo[4,5-c]quinolin-1-yl)-phenyl]-propionitrile
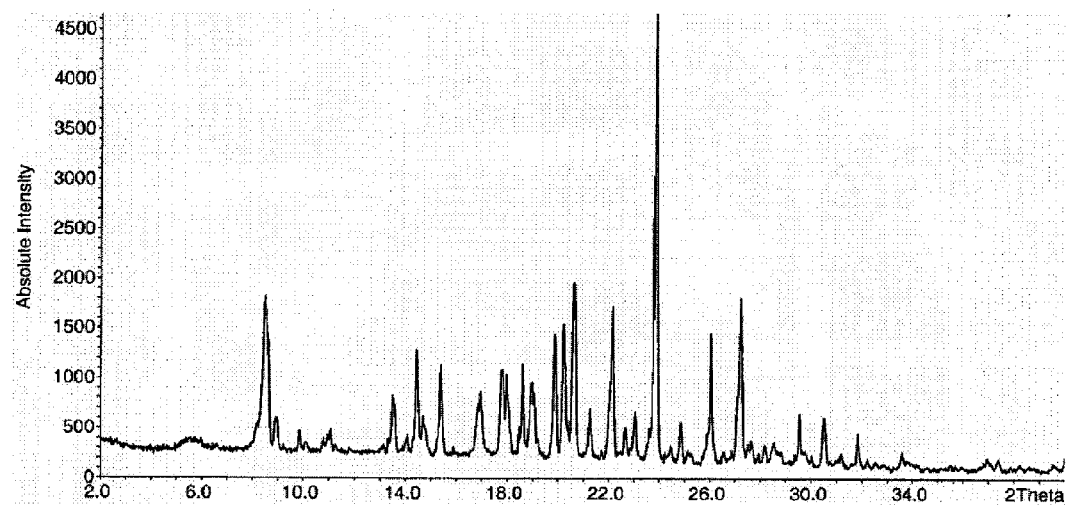

FIG. 5 Form H$_A$ of 2-methyl-2-[4-(3-methyl-2-oxo-8-quinolin-3-yl-2,3-dihydro-imidazo[4,5-c]quinolin-1-yl)-phenyl]-propionitrile monohydrate
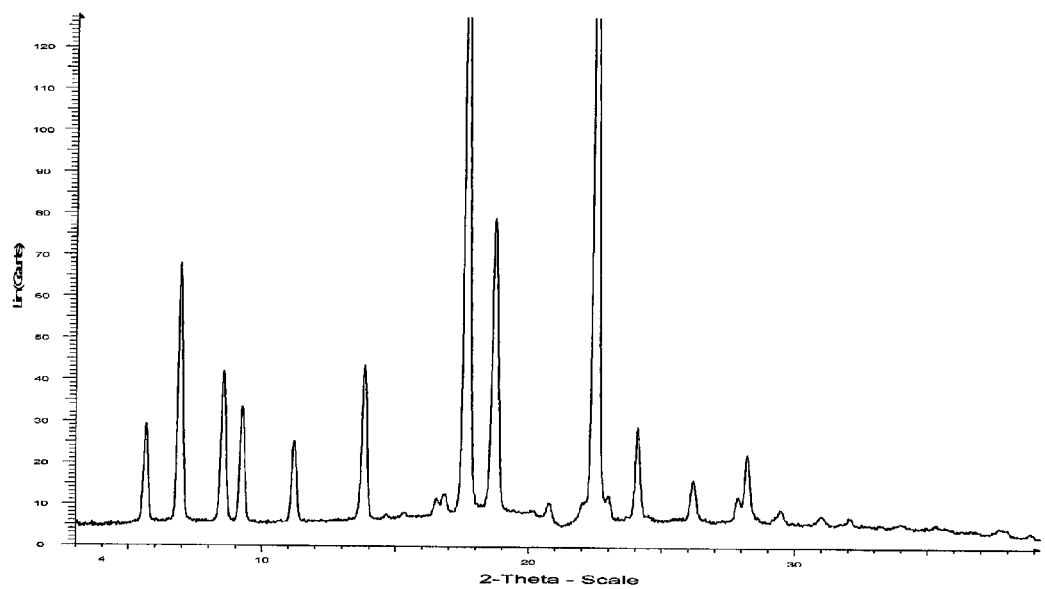

FIG. 6  Form A of 2-methyl-2-[4-(3-methyl-2-oxo-8-quinolin-3-yl-2,3-dihydro-imidazo[4,5-c]quinolin-1-yl)-phenyl]-propionitrile monotosylate
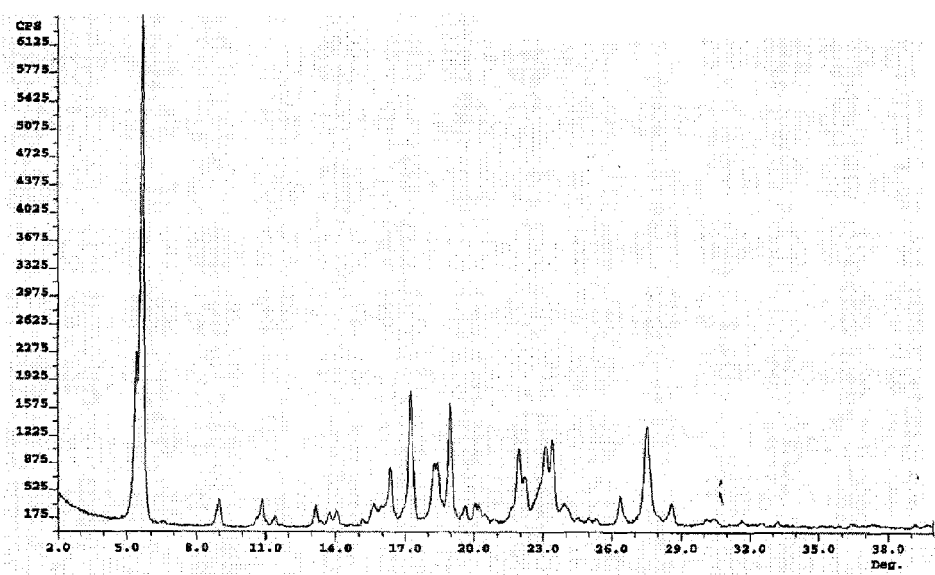

FIG. 7  Form B of 2-methyl-2-[4-(3-methyl-2-oxo-8-quinolin-3-yl-2,3-dihydro-imidazo[4,5-c]quinolin-1-yl)-phenyl]-propionitrile monotosylate
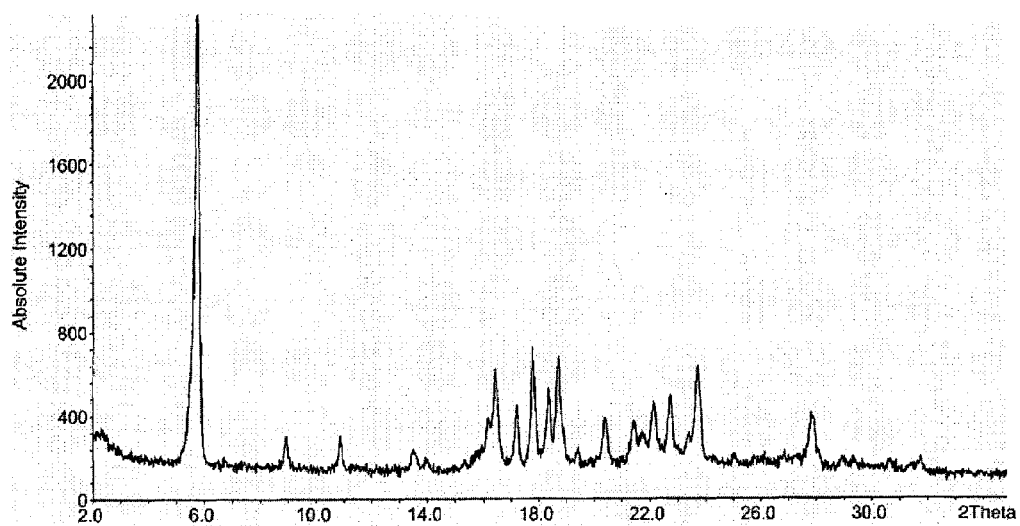

FIG. 8  Form H$_A$ of 2-methyl-2-[4-(3-methyl-2-oxo-8-quinolin-3-yl-2,3-dihydro-imidazo[4,5-c]quinolin-1-yl)-phenyl]-propionitrile monotosylate monohydrate
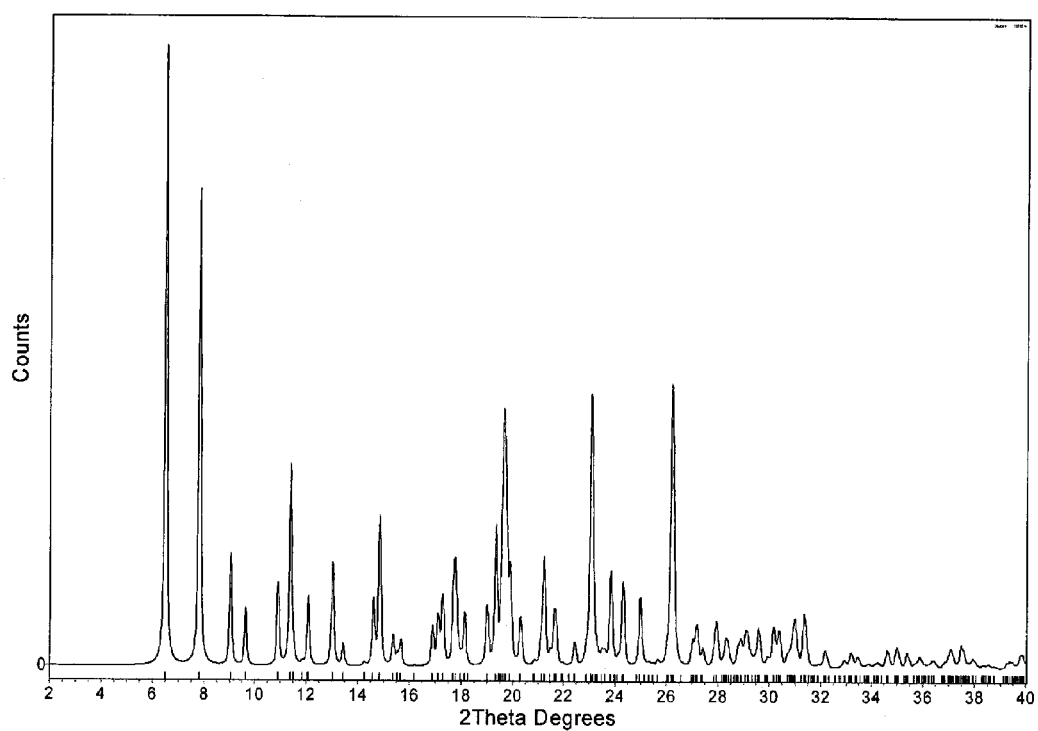

FIG. 9  Form H$_B$ of 2-methyl-2-[4-(3-methyl-2-oxo-8-quinolin-3-yl-2,3-dihydro-imidazo[4,5-c]quinolin-1-yl)-phenyl]-propionitrile monotosylate dihydrate
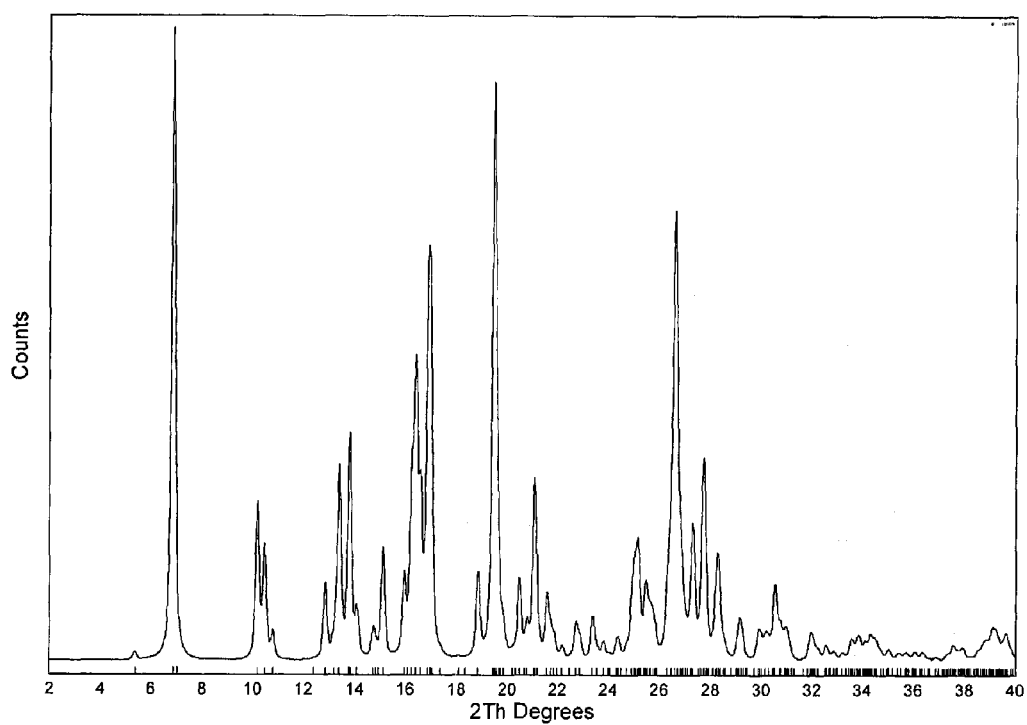

FIG. 10 Form S_A of 2-methyl-2-[4-(3-methyl-2-oxo-8-quinolin-3-yl-2,3-dihydro-imidazo[4,5-c]quinolin-1-yl)-phenyl]-propionitrile monotosylate diformic acid solvate
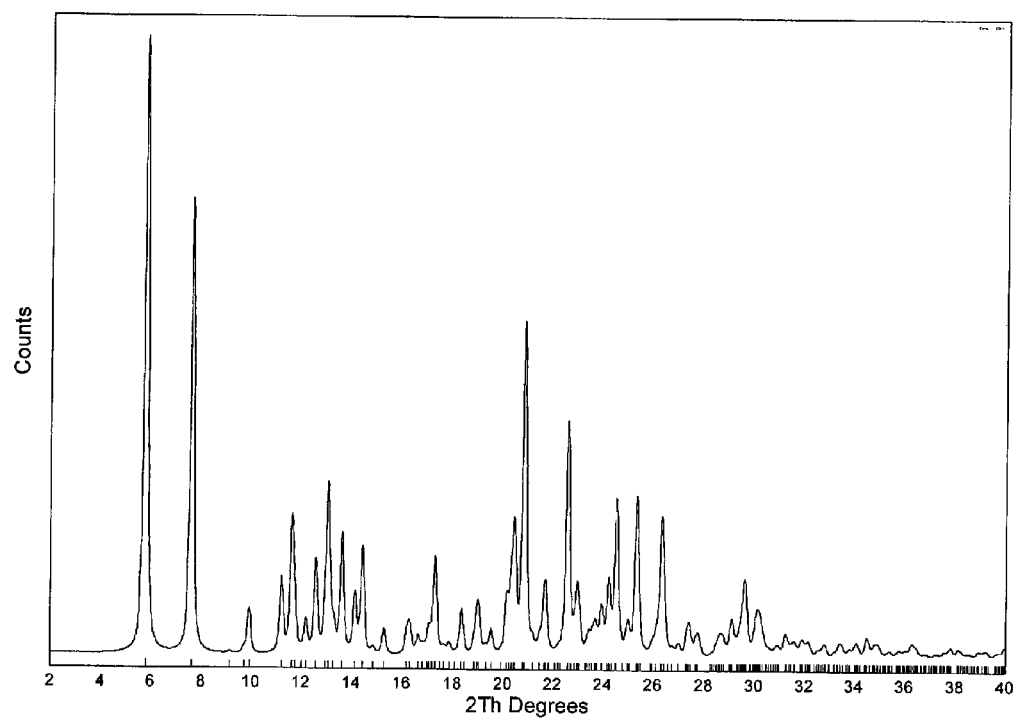

FIG. 11  Form A of 2-methyl-2-[4-(3-methyl-2-oxo-8-quinolin-3-yl-2,3-dihydro-imidazo[4,5-c]quinolin-1-yl)-phenyl]-propionitrile ditosylate
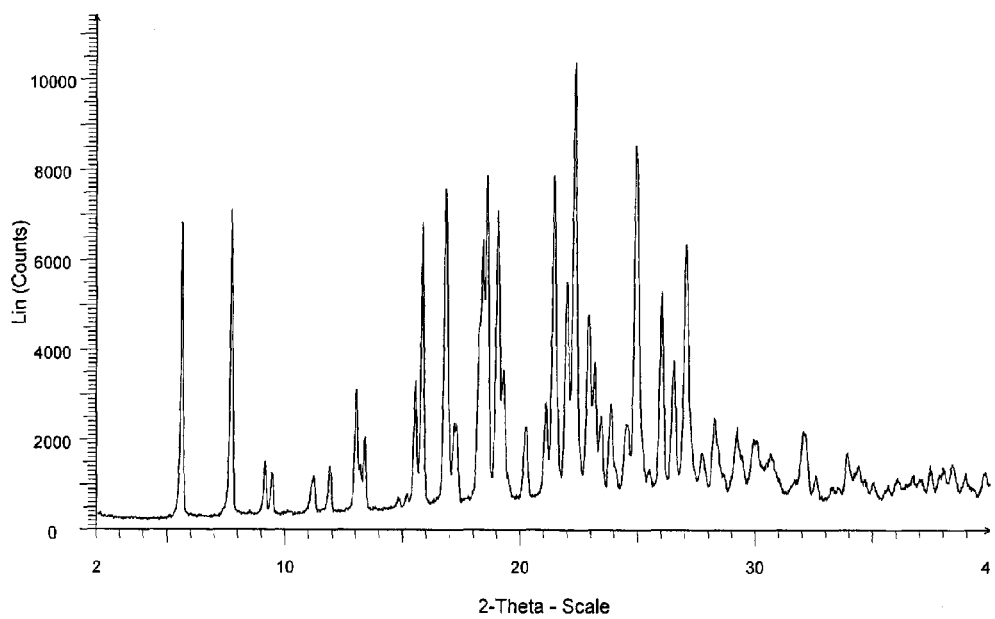

FIG. 12 Form H$_A$ of 2-methyl-2-[4-(3-methyl-2-oxo-8-quinolin-3-yl-2,3-dihydro-imidazo[4,5-c]quinolin-1-yl)-phenyl]-propionitrile ditosylate trihydrate
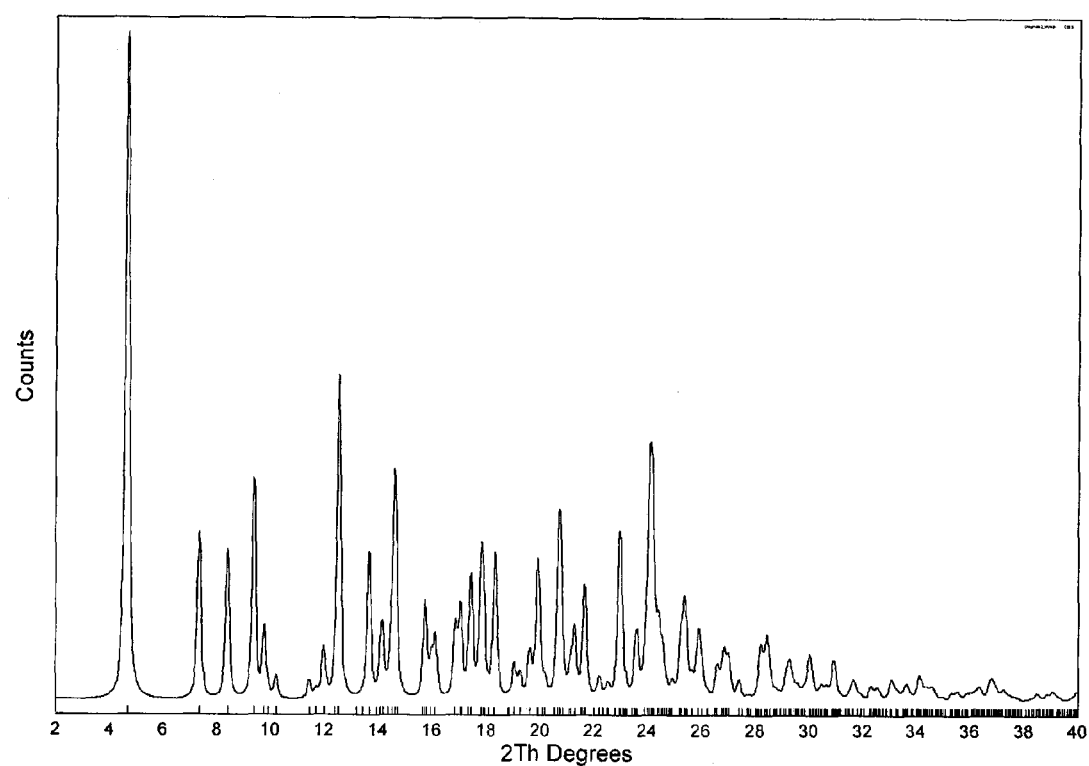

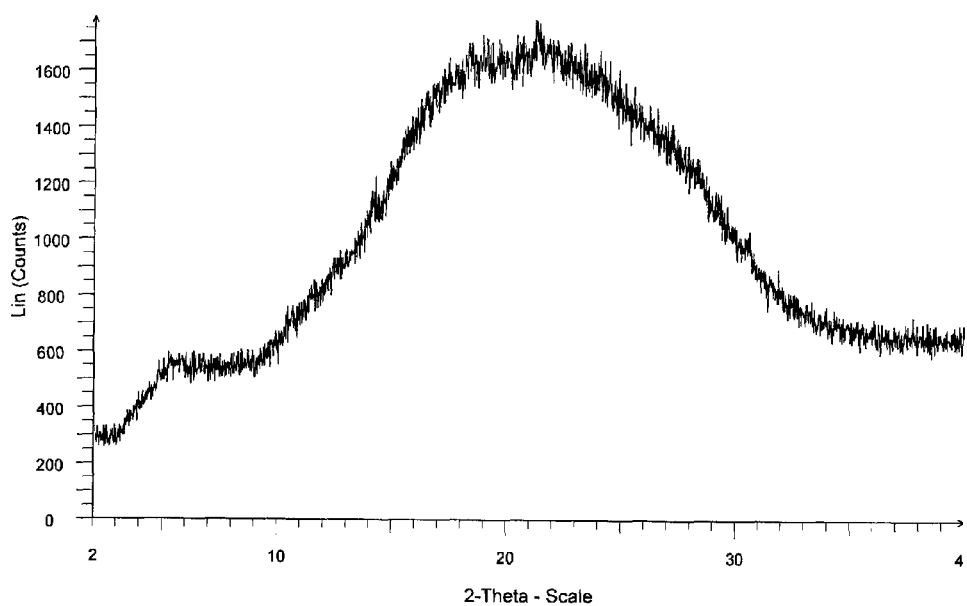
FIG. 13 Amorphous form of 2-methyl-2-[4-(3-methyl-2-oxo-8-quinolin-3-yl-2,3-dihydro-imidazo[4,5-c]quinolin-1-yl)-phenyl]-propionitrile monotosylate FIG. 14 Raman spectra of amorphous form of 2-methyl-2-[4-(3-methyl-2-oxo-8-quinolin-3-yl-2,3-dihydro-imidazo[4,5-c]quinolin-1-yl)-phenyl]-propionitrile monotosylate
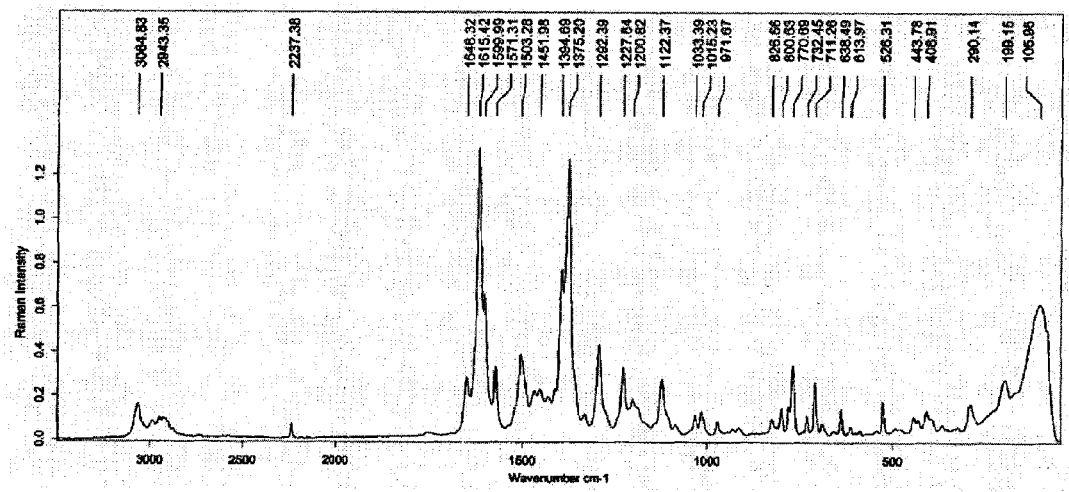

FIG. 15  FT-IR spectra of amorphous form of 2-methyl-2-[4-(3-methyl-2-oxo-8-quinolin-3-yl-2,3-dihydro-imidazo[4,5-c]quinolin-1-yl)-phenyl]-propionitrile monotosylate
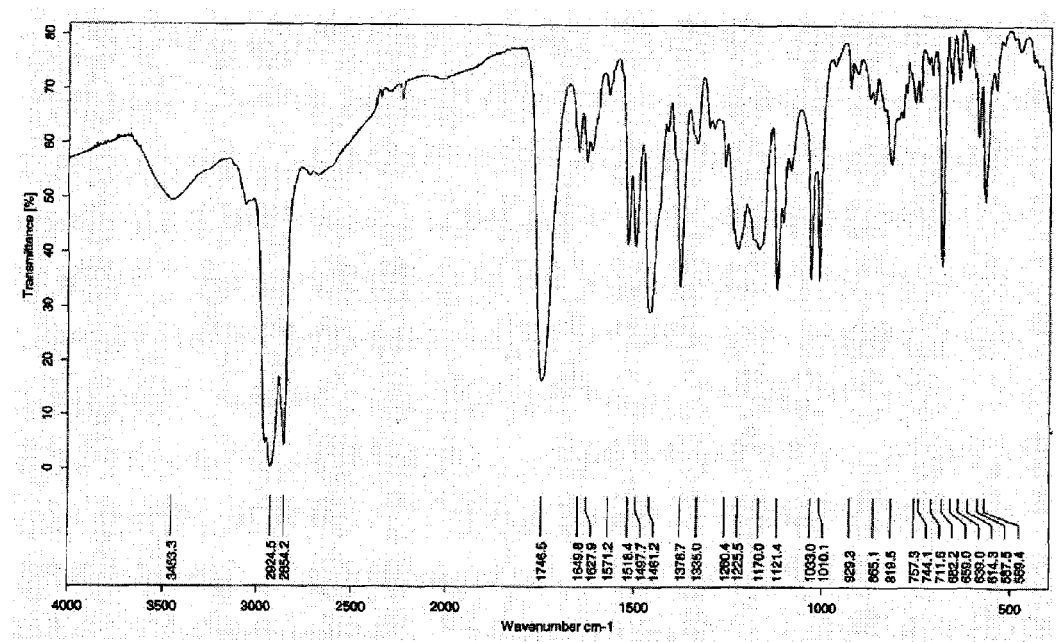

FIG. 16 Form $S_C$ of 2-methyl-2-[4-(3-methyl-2-oxo-8-quinolin-3-yl-2,3-dihydro-imidazo[4,5-c]quinolin-1-yl)-phenyl]-propionitrile monotosylate diformic acid solvate monohydrate
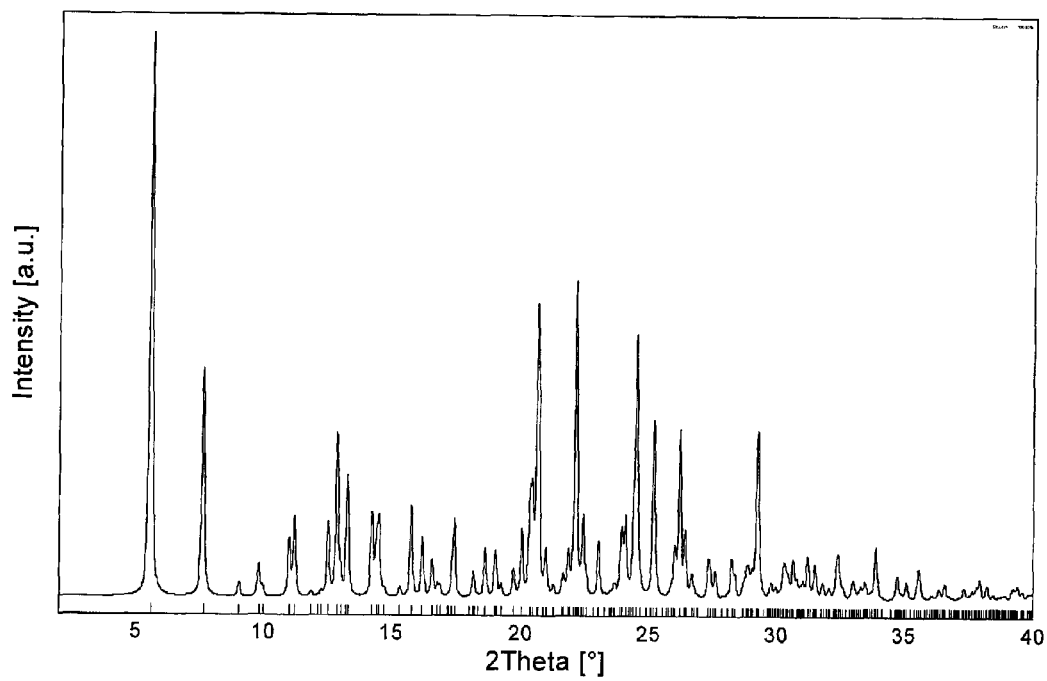

FIG. 17 Form $S_B$ of 2-methyl-2-[4-(3-methyl-2-oxo-8-quinolin-3-yl-2,3-dihydro-imidazo[4,5-c]quinolin-1-yl)-phenyl]-propionitrile monotosylate diacetic acid solvate
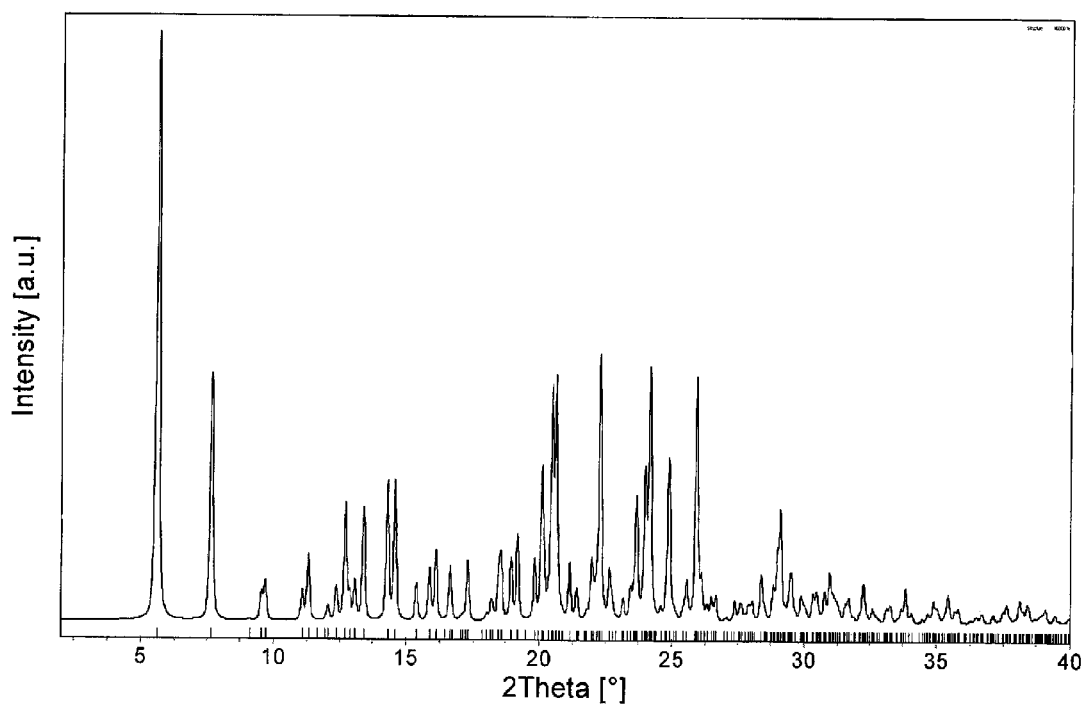

SALTS AND CRYSTALL FORMS OF 2-METHYL-2-[4-(3-METHYL-2-OXO-8-QUINOLIN-3-YL-2,3-DIHYDRO-IMIDAZO[4,5-C]QUINOLIN-1-YL)-PHENYL]-PROPIONITRILE

This is a National Stage of International Application No. PCT/US2007/084893 filed Nov. 16, 2007, which claims benefit of U.S. Provisional Application No. 60/866,483 filed Nov. 20, 2006, which in its entirety are herein incorporated by reference.

The invention relates to particular solid, preferably crystalline or amorphous, especially crystalline, forms of 2-methyl-2-[4-(3-methyl-2-oxo-8-quinolin-3-yl-2,3-dihydro-imidazo[4,5-c]quinolin-1-yl)-phenyl]-propionitrile (compound I, see below), its hydrates and solvates, its salts and hydrates and solvates of its salts, certain processes for their preparation, pharmaceutical compositions containing these solid forms, and their use in diagnostic methods or, preferably, for the therapeutic treatment of warm-blooded animals, especially humans, and their use as an intermediate or for the preparation of pharmaceutical preparations for use in diagnostic methods or, preferably, for the therapeutic treatment of warm-blooded animals, especially humans.

BACKGROUND OF THE INVENTION 2-methyl-2-[4-(3-methyl-2-oxo-8-quinolin-3-yl-2,3-dihydro-imidazo[4,5-c]quinolin-1-yl)-phenyl]-propionitrile, its inhibition of the activity of the lipid kinases, such as the PI3-kinase and/or members of the PI3-kinase-related protein kinase family (also called PIKK and include DNA-PK, ATM, ATR, hSMG-1 and mTOR), such as the DNA protein-kinase; its preparation; and its use, especially as an anti-tumour agent, are described in WO2006/122806. The compound is exemplified therein in free form (see for instance Example 7) and as 4-toluenesulfonic acid salt in a stoichiometric ratio of 1:1. The synthesis of 2-methyl-2-[4-(3-methyl-2-oxo-8-quinolin-3-yl-2,3-dihydro-imidazo[4,5-c]quinolin-1-phenyl]-propionitrile is also described in the experimental part as Example 1.

It has now been surprisingly found that under certain conditions new particular crystalline forms of 2-methyl-2-[4-(3-methyl-2-oxo-8-quinolin-3-yl-2,3-dihydro-imidazo[4,5-c]quinolin-1-yl)-phenyl]-propionitrile, its hydrates and solvates, its salts and hydrates or solvates of its salts may be found, which are described hereinafter, and which have advantageous utilities and properties. They exhibit new physical properties which may have substantial differences in certain pharmaceutical properties and which can be utilized in drug substance and drug product development; e.g. for the dissolution of drug substances and/or facilitated routes of manufacturing/purification.

DETAILED DESCRIPTION OF THE INVENTION

The invention is described in more detail in the following with the help of drawings and other aids.

The invention relates especially to essentially pure crystal forms of 2-methyl-2-[4-(3-methyl-2-oxo-8-quinolin-3-yl-2,3-dihydro-imidazo[4,5-c]quinolin-1-yl)-phenyl]-propionitrile of formula I (compound I),

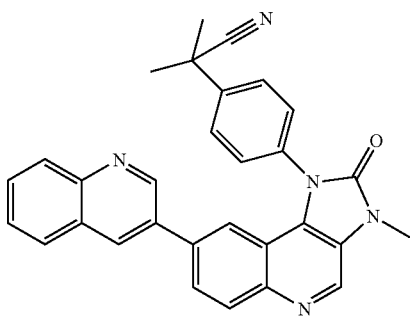 [SMILES: Cn1c(=O)n(-c2ccc(C(C)(C)C#N)cc2)c2c3cc(-c4cnc5ccccc5c4)ccc3ncc21]

of a hydrate or solvate of the compound of formula I, or of a salt of the compound of formula I, or of a hydrate or solvate of a salt of the compound of formula I.

DESCRIPTION OF THE DRAWINGS

In the X-ray diagrams discussed below, the angle of diffraction 2Theta is plotted on the horizontal axis (x-axis) and the intensity (counts) on the vertical (y-axis).

FIG. 1 Form A of 2-methyl-2-[4-(3-methyl-2-oxo-8-quinolin-3-yl-2,3-dihydro-imidazo[4,5-c]quinolin-1-yl)-phenyl]-propionitrile The strongest line in the X-ray diffraction diagram is observed at an angle of diffraction 2Theta of 8.4° having a relative intensity of 100%. Two further lines were observed having a relative intensity of more than 10% at 7.9° and 10.5°. More broadly, this form is characterized by diffractions peaks at angles of diffraction 2Theta of 7.9°, 8.4°, 10.5°, 10.9°, 13.3°, 17.9°, 22.0°. X-ray powder data measured with Scintag instrument with Cu K alpha radiation source; Step 0.020°, Range 2.00-40.00 (Deg.), Const. Scan Rate 0.50 Deg/min (all 2Theta values+/−0.3).

FIG. 2 Form B of 2-methyl-2-[4-(3-methyl-2-oxo-8-quinolin-3-yl-2,3-dihydro-imidazo[4,5-c]quinolin-1-yl)-phenyl]-propionitrile The strongest line in the X-ray diffraction diagram is observed at an angle of diffraction 2Theta of 6.9° having a relative intensity of 100%. Two further lines were observed having a relative intensity of more than 10% at 14.2° and 17.7°. More broadly, this form is characterized by diffractions peaks at angles of diffraction 2Theta of 6.9°, 8.7°, 10.1°, 14.2°, 17.7°, 20.5°, 21.1°. X-ray powder data measured with Scintag instrument with Cu K alpha radiation source; Step 0.020°, Range 2.00-40.00 (Deg.), Const. Scan Rate 0.50 Deg/min (all 2Theta values+/−0.3).

FIG. 3 Simulated X-ray powder pattern of form C of 2-methyl-2-[4-(3-methyl-2-oxo-8-quinolin-3-yl-2,3-dihydro-imidazo[4,5-c]quinolin-1-yl)-phenyl]-propionitrile The strongest line in the X-ray diffraction diagram is observed at an angle of diffraction 2Theta of 14.7° having a relative intensity of 100%. Two further lines were observed having a relative intensity of more than 10% at 11.4° and 18.6°. More broadly, this form is characterized by diffractions peaks at angles of diffraction 2Theta of 6.6°, 11.4°, 14.7°, 15.6°, 18.3°, 18.6°, 19.8°, 22.7°, 24.5° (all 2Theta values+/−0.3).

FIG. 4 Form D of 2-methyl-2-[4-(3-methyl-2-oxo-8-quinolin-3-yl-2,3-dihydro-imidazo[4,5-c]quinolin-1-yl)-phenyl]-propionitrile The strongest line in the X-ray diffraction diagram is observed at an angle of diffraction 2Theta of 23.9° having a relative intensity of 100%. Two further lines were observed having a relative intensity of more than 10% at 20.6° and 22.1°. More broadly, this form is characterized by diffractions peaks at angles of diffraction 2Theta of 8.5°, 19.9°, 20.2°, 20.6°, 22.1°, 23.9°, 26.1°, 27.2°. X-ray powder data measured with STOE Stadi P Combi instrument with Cu K alpha1 radiation source; Slit 4 mm/2 mm; transmission between kapton foil; Monochrom.: Curved Germanium (111), Radiation 1.54060 Å, Generator: 50 kV, 30 mA, Detector: Linear PSD/Moving/Fixed Omega; Range 1: 2Theta (begin, end, step)=2.000, 39.980, 0.020; 390.00 s/step (all 2Theta values+/−0.3).

FIG. 5 Form $H_A$ of 2-methyl-2-[4-(3-methyl-2-oxo-8-quinolin-3-yl-2,3-dihydro-imidazo[4,5-c]quinolin-1-yl)-phenyl]-propionitrile monohydrate The strongest line in the X-ray diffraction diagram is observed at an angle of diffraction 2Theta of 17.6° having a relative intensity of 100%. Two further lines were observed having a relative intensity of more than 10% at 18.8° and 22.5°. More broadly, this form is characterized by diffractions peaks at angles of diffraction 2Theta of 5.6°, 6.9°, 8.5°, 9.2°, 13.8°, 17.6°, 18.8°, 22.5°, 24.0°. X-ray powder data measured with Bruker D8 Discover GADDS in reflection geometry (all 2Theta values+/−0.3).

FIG. 6 Form A of 2-methyl-2-[4-(3-methyl-2-oxo-8-quinolin-3-yl-2,3-dihydro-imidazo[4,5-c]quinolin-1-yl)-phenyl]-propionitrile monotosylate The strongest line in the X-ray diffraction diagram is observed at an angle of diffraction 2Theta of 5.7° having a relative intensity of 100%. Two further lines were observed having a relative intensity of more than 10% at 5.4° and 17.2°. More broadly, this form is characterized by diffractions peaks at angles of diffraction 2Theta of 5.4°, 5.7°, 16.4°, 17.2°, 18.3°, 19.0°, 22.0°, 23.1°, 23.4°, 27.5°. X-ray powder data measured with Scintag instrument with Cu K alpha radiation source; Step 0.020°, Range 2.00-40.00 (Deg.), Const. Scan Rate 0.50 Deg/min (all 2Theta values+/−0.3).

FIG. 7 Form B of 2-methyl-2-[4-(3-methyl-2-oxo-8-quinolin-3-yl-2,3-dihydro-imidazo[4,5-c]quinolin-1-yl)-phenyl]-propionitrile monotosylate The strongest line in the X-ray diffraction diagram is observed at an angle of diffraction 2Theta of 5.8° having a relative intensity of 100%. Two further lines were observed having a relative intensity of more than 10% at 17.8° and 18.7°. More broadly, this form is characterized by diffractions peaks at angles of diffraction 2Theta of 5.8°, 16.4°, 17.2°, 17.8°, 18.4°, 18.7°, 22.1°, 22.7°, 23.7°. X-ray powder data measured with STOE Stadi P Combi instrument with Cu K alpha1 radiation source; Slit 4 mm/2 mm; transmission between kapton foil; Monochrom.: Curved Germanium (111), Radiation 1.54060 Å, Generator: 50 kV, 30 mA, Detector: Linear PSD/Moving/Fixed Omega; Range 1: 2Theta (begin, end, step)=2.000, 39.980, 0.020; 390.00 s/step (all 2Theta values+/−0.3).

FIG. 8 Simulated X-ray powder pattern of form $H_A$ of 2-methyl-2-[4-(3-methyl-2-oxo-8-quinolin-3-yl-2,3-dihydro-imidazo[4,5-c]quinolin-1-yl)-phenyl]-propionitrile monotosylate monohydrate (calculated from the corresponding single crystal structure)

Crystallographic Data of Compound I Monotosylate Monohydrate:

| Crystal system | Monoclinic |
| --- | --- |
| Space group | P2$_1$/c |
| a, Å | 9.790 (3) |
| b, Å | 12.431 (3) |

-continued

| c, Å | 27.209 (8) |
| --- | --- |
| α, β, γ | 90, 92.560 (16), 90 |
| V, Å$^3$ | 3308.0 (16) |
| D$_{calc}$, g cm$^{-3}$ | 1.325 |
| Z | 4 |

The strongest line in the X-ray diffraction diagram is observed at an angle of diffraction 2Theta of 6.5° having a relative intensity of 100%. Four further lines were observed having a relative intensity of more than 50% at 7.8°, 19.6°, 23.1° and 26.2°. More broadly, this form is characterized by diffractions peaks at angles of diffraction 2Theta of 6.5°, 7.8°, 9.0°, 11.4°, 14.9°, 19.3°, 19.6°, 23.1°, 26.2° (all 2Theta values+/−0.3).

FIG. 9 Simulated X-ray powder pattern of form $H_B$ of 2-methyl-2-[4-(3-methyl-2-oxo-8-quinolin-3-yl-2,3-dihydro-imidazo[4,5-c]quinolin-1-yl)-phenyl]-propionitrile monotosylate dihydrate (calculated from the corresponding single crystal structure)

Crystallographic Data of Compound I Monotosylate Dihydrate:

| Crystal system | Triclinic |
| --- | --- |
| Space group | P-1 |
| a, Å | 7.1921 (2) |
| b, Å | 13.8439 (3) |
| c, Å | 17.5657 (4) |
| α, β, γ | 111.203 (1), 90.980 (1), 96.388 (1) |
| V, Å$^3$ | 1617.33 (7) |
| D$_{calc}$, g cm$^{-3}$ | 1.318 |
| Z | 2 |

The strongest line in the X-ray diffraction diagram is observed at an angle of diffraction 2Theta of 6.9° having a relative intensity of 100%. Two further lines were observed having a relative intensity of more than 10% at 19.5° and 26.6°. More broadly, this form is characterized by diffractions peaks at angles of diffraction 2Theta of 6.9°, 10.2°, 13.4°, 13.8°, 16.4°, 16.9°, 19.5°, 21.1°, 26.6° (all 2Theta values+/−0.3).

FIG. 10 Simulated X-ray powder pattern of form $S_A$ of 2-methyl-2-[4-(3-methyl-2-oxo-8-quinolin-3-yl-2,3-dihydro-imidazo[4,5-c]quinolin-1-yl)-phenyl]-propionitrile monotosylate diformic acid solvate (calculated from the corresponding single crystal structure)

Crystallographic Data of Compound I Monotosylate Formic Acid Solvate:

| Crystal system | Monoclinic |
| --- | --- |
| Space group | P2$_1$/n |
| a, Å | 9.4104 (3) |
| b, Å | 12.5101 (5) |
| c, Å | 30.3995 (11) |
| α, β, γ | 90, 92.183 (2), 90 |
| V, Å$^3$ | 3576.2 (2) |
| D$_{calc}$, g cm$^{-3}$ | 1.547 |
| Z | 4 |

The strongest line in the X-ray diffraction diagram is observed at an angle of diffraction 2Theta of 5.8° having a relative intensity of 100%. Two further lines were observed having a relative intensity of more than 10% at 7.6° and 20.9°. More broadly, this form is characterized by diffractions peaks at angles of diffraction 2Theta of 5.8°, 7.9°, 11.7°, 13.1°, 13.6°, 14.5°, 17.3°, 20.9°, 22.6°, 24.5° (all 2Theta values+/−0.3).

FIG. 11 Form A of 2-methyl-2-[4-(3-methyl-2-oxo-8-quinolin-3-yl-2,3-dihydro-imidazo[4,5-c]quinolin-1-yl)-phenyl]-propionitrile ditosylate Crystallographic Data of Compound I Ditosylate:

| Crystal system | Monoclinic |
|---|---|
| Space group | P2$_1$/n |
| a, Å | 10.3246 (2) |
| b, Å | 12.0935 (3) |
| c, Å | 31.5031 (7) |
| α, β, γ | 90, 99.416 (1), 90 |
| V, Å$^3$ | 3880.50 (15) |
| D$_{calc}$, g cm$^{-3}$ | 1.159 |
| Z | 4 |

The strongest line in the X-ray diffraction diagram is observed at an angle of diffraction 2Theta of 22.4° having a relative intensity of 100%. Two further lines were observed having a relative intensity of more than 10% at 21.5° and 25.0°. More broadly, this form is characterized by diffractions peaks at angles of diffraction 2Theta of 5.6°, 7.7°, 15.8°, 16.8°, 18.6°, 19.1°, 21.5°, 22.4°, 25.0°. X-ray powder data measured with Bruker D8 Advance instrument with Cu K alpha radiation source; Step 0.017°, Cnt. time 0.3 s., Range 2.00-40.00 (Deg.), variable divergence slit 12 mm, VANTEC PSD detector (all 2Theta values+/−0.3).

FIG. 12 Simulated X-ray powder pattern of form H$_A$ of 2-methyl-2-[4-(3-methyl-2-oxo-8-quinolin-3-yl-2,3-dihydro-imidazo[4,5-c]quinolin-1-yl)-phenyl]-propionitrile ditosylate trihydrate (calculated from the corresponding single crystal structure)

Crystallographic Data of Compound I Ditosylate Trihydrate:

| Crystal system | Monoclinic |
|---|---|
| Space group | P2$_1$/n |
| a, Å | 9.120 (3) |
| b, Å | 12.646 (4) |
| c, Å | 37.827 (12) |
| α, β, γ | 90, 95.565 (16), 90 |
| V, Å$^3$ | 4342 (2) |
| D$_{calc}$, g cm$^{-3}$ | 1.328 |
| Z | 4 |

The strongest line in the X-ray diffraction diagram is observed at an angle of diffraction 2Theta of 4.7° having a relative intensity of 100%. Two further lines were observed having a relative intensity of more than 10% at 9.4° and 12.6°. More broadly, this form is characterized by diffractions peaks at angles of diffraction 2Theta of 4.7°, 7.4°, 8.4°, 9.4°, 12.6°, 13.7°, 14.7°, 18.3°, 20.8°, 24.1° (all 2Theta values+/−0.3).

FIG. 13 Amorphous form of 2-methyl-2-[4-(3-methyl-2-oxo-8-quinolin-3-yl-2,3-dihydro-imidazo[1,5-c]quinolin-1-yl)-phenyl]-propionitrile monotosylate X-ray powder data measured with Bruker D8 Advance instrument with Cu K alpha radiation source; Step 0.017°, Cnt. time 0.3 s., Range 2.00-40.00 (Deg.), variable divergence slit 12 mm, VANTEC PSD detector.

FIG. 14 Raman spectra of amorphous form of 2-methyl-2-[4-(3-methyl-2-oxo-8-quinolin-3-yl-2,3-dihydro-imidazo[4,5-c]quinolin-1-yl)-phenyl]-propionitrile monotosylate Raman spectrum of the sample measured by dispersive Raman spectrometer with 1064 nm laser excitation source (Bruker RFS 100). The significant bands in the spectra are expressed in reciprocal wave numbers (cm$^{-1}$).

FIG. 15 FT-IR spectra of amorphous form of 2-methyl-2-[4-(3-methyl-2-oxo-8-quinolin-3-yl-2,3-dihydro-imidazo[4,5-c]quinolin-1-yl)-phenyl]-propionitrile monotosylate The infrared absorption spectrum for the sample obtained using Fourier Transform Infrared Microscope (Bruker Vertex 70). The significant bands in the spectra are expressed in reciprocal wave numbers (cm$^{-1}$).

FIG. 16 Simulated X-ray powder pattern of form S$_C$ of 2-methyl-2-[4-(3-methyl-2-oxo-8-quinolin-3-yl-2,3-dihydro-imidazo[4,5-c]quinolin-1-yl)-phenyl]-propionitrile monotosylate diformic acid solvate monohydrate (calculated from the corresponding single crystal structure)

Crystallographic Data of Compound I Monotosylate Formic Acid Solvate Monohydrate:

| Crystal system | Monoclinic |
|---|---|
| Space group | P2$_1$/n |
| a, Å | 9.304 (3) |
| b, Å | 12.421 (4) |
| c, Å | 31.500 (10) |
| α, β, γ | 90, 91.571 (18), 90 |
| V, Å$^3$ | 3639 (2) |
| D$_{calc}$, g cm$^{-3}$ | 1.372 |
| Z | 4 |

The strongest line in the X-ray diffraction diagram is observed at an angle of diffraction 2Theta of 5.6° having a relative intensity of 100%. Two further lines were observed having a relative intensity of more than 10% at 20.7° and 22.2°. More broadly, this form is characterized by diffractions peaks at angles of diffraction 2Theta of 5.6°, 7.6°, 12.9°, 13.3°, 14.3°, 20.7°, 22.2°, 24.5°, 25.2°, 26.2°, 29.3 (all 2Theta+/−0.3).

FIG. 17 Simulated X-ray powder pattern of form S$_B$ of 2-methyl-2-[4-(3-methyl-2-oxo-8-quinolin-3-yl-2,3-dihydro-imidazo[4,5-c]quinolin-1-yl)-phenyl]-propionitrile monotosylate diacetic acid solvate (calculated from the corresponding single crystal structure)

Crystallographic Data of Compound I Monotosylate Acetic Acid Solvate:

| Crystal system | Monoclinic |
|---|---|
| Space group | P2$_1$/n |
| a, Å | 9.590 (2) |
| b, Å | 12.372 (3) |
| c, Å | 31.220 (8) |
| α, β, γ | 90, 91.487 (11), 90 |
| V, Å$^3$ | 3702.9 (15) |
| D$_{calc}$, g cm$^{-3}$ | 1.367 |
| Z | 4 |

The strongest line in the X-ray diffraction diagram is observed at an angle of diffraction 2Theta of 5.7° having a relative intensity of 100%. Two further lines were observed having a relative intensity of more than 10% at 7.7° and 22.3°. More broadly, this form is characterized by diffractions peaks at angles of diffraction 2Theta of 5.7°, 7.7°, 12.7°, 13.4°, 14.3°, 14.6°, 20.1°, 20.5°, 20.7°, 22.3°, 23.7°, 24.0°, 24.9°, 26.0° (all 2Theta values+/−0.3).

The term "essentially pure" is understood in the context of the present invention to mean especially that at least 90, preferably at least 95, and most preferably at least 99 percent by weight of the crystals of the compound of formula I, its hydrates or solvates, its salts or hydrates or solvates of its salts are present in the specified crystal form according to the invention.

The term "solid form" according to the present invention includes crystalline forms and amorphous forms. Preferred solid forms are crystalline forms In the context with stating that a crystal form of the compound of formula I, its hydrates or solvates, its salts or its hydrates or solvates of its salts exhibits an X-ray diffraction diagram essentially as outlined in one of the Figures, the term "essentially" means that at least the major lines of the diagram depicted in said Figure, i.e. those having a relative line intensity of more than 20%, especially more than 30%, as compared to the most intense line in the diagram, have to be present.

In one preferred embodiment, the crystal form of the compound of formula I, its hydrates or solvates, its salts or its hydrates or solvates of its salts exhibits an X-ray diffraction diagram essentially as outlined in one of the Figures.

Of particularly high preference are solid, preferably crystalline, form of the compound of formula I, its hydrates and solvates, its salts and hydrates or solvates of its salts obtainable as described in the Examples.

One of the advantages of having access to different crystal forms of the compound of formula I, its hydrates or solvates, its salts or hydrates or solvates of its salts is the fact that distinct crystal forms are prone to incorporate distinct impurities upon crystallization, i.e. an impurity incorporated in crystal form AA is not necessarily also incorporated in the crystal form BB or in the crystal form CC. With other words, preparing consecutively distinct crystal forms of the same material increases the purity of the finally obtained substance. Furthermore, distinct crystal forms display different physical properties such as melting points, hygroscopicities, solubilities, flow properties or thermodynamic stabilities, and, hence, distinct crystal forms allow the choice of the most suitable form for a certain use or aspect, e.g. the use as an intermediate in the process of drug manufacture or in distinct administration forms like tablets, capsules, ointments or solutions.

The solid, preferably crystalline, forms of the compound of formula I, its hydrates or solvates, its salts and hydrates or solvates of its salts possess valuable pharmacological properties and may, for example, be used in the treatment of conditions which are mediated by the activation of the PI3 kinase enzymes, such as proliferative, inflammatory or allergic conditions, or disorders commonly occurring in connection with transplantation.

The solid, amorphous or crystalline, preferably crystalline, forms of the compound of formula I, its hydrates or solvates, its salts and hydrates or solvates of its salts may preferably used in the treatment of a proliferative disease selected from a benign or malignant tumor, carcinoma of the brain, kidney, liver, adrenal gland, bladder, breast, stomach, gastric tumors, ovaries, colon, rectum, prostate, pancreas, lung, vagina or thyroid, sarcoma, glioblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, lymphomas, a mammary carcinoma or a leukemia. Other diseases include Cowden syndrome, Lhermitte-Dudos disease and Bannayan-Zonana syndrome, or diseases in which the PI3K/PKB pathway is aberrantly activated.

The present invention relates especially to form A of 2-methyl-2-[4-(3-methyl-2-oxo-8-quinolin-3-yl-2,3-dihydro-imidazo[4,5-c]quinolin-1-yl)-phenyl]-propionitrile monotosylate in the treatment of one of the said diseases mentioned herein or in the preparation of a pharmacological agent for the treatment thereof.

The invention relates also to a method for the treatment of warm-blooded animals suffering from said diseases, wherein a quantity of the solid, preferably crystalline, form of the compound of formula I, its hydrates or solvates, its salts or hydrates or solvates of its salts which is effective against the disease concerned, especially a quantity with antiproliferative efficacy, is administered to warm-blooded animals in need of such treatment. The invention relates moreover to the use of solid, preferably crystalline, forms of the compound of formula I, its hydrates or solvates, its salts and hydrates or solvates of its salts for the preparation of pharmaceutical compositions for use in treating the human or animal body, especially for the treatment of proliferative disease, such as benign or malignant tumor, carcinoma of the brain, kidney, liver, adrenal gland, bladder, breast, stomach, gastric tumors, ovaries, colon, rectum, prostate, pancreas, lung, vagina or thyroid, sarcoma, glioblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, lymphomas, a mammary carcinoma or a leukemia.

The solid, preferably crystalline, forms of the compound of formula I, its hydrates or solvates, its salts or hydrates or solvates of its salts described herein can be utilized to prepare stable pharmaceutical dosage forms. Hence, the invention relates also to pharmaceutical preparations which contain an amount, especially an therapeutically effective amount for prevention or treatment of one of the diseases mentioned herein, of the solid, preferably crystalline, form of the compound of formula I, its hydrates or solvates, its salts or hydrates or solvates of its salts, together with pharmaceutically acceptable carriers which are suitable for topical, enteral, for example oral or rectal, or parenteral administration and may be inorganic or organic and solid or liquid.

The present pharmaceutical preparations which, if so desired, may contain further pharmacologically active substances, are prepared in a manner known per se, for example by means of conventional mixing, granulating, coating, dissolving or lyophilising processes, and contain from about 1% to 100%, especially from about 1% to about 20%, of the active substance or substances.

The present invention relates also to a process for the preparation of a pharmaceutical composition which comprises mixing a solid, preferably crystalline, form of the compound of formula I, its hydrates or solvates, its salts or hydrates or solvates of its salts of the invention together with at least one pharmaceutically acceptable carrier or diluent.

The term "pharmaceutical composition" is intended to encompass a product comprising the active ingredient(s), pharmaceutically acceptable excipients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing the active ingredient, optionally additional active ingredient(s) and pharmaceutically acceptable excipients.

The term "excipient" means a component of a pharmaceutical product that is not the active ingredient, such as filler, diluent and carrier. The excipients that are useful in preparing a pharmaceutical composition are preferably generally safe, non-toxic and neither biologically nor otherwise undesirable, and are acceptable for veterinary use, as well as human pharmaceutical use. "A pharmaceutically acceptable excipient", as used in the specification and claims, includes both one and more than one such excipient.

"Therapeutically effective amount" means the amount of a compound that, when administered for treating or preventing a disease, is sufficient to effect such treatment or prevention for the disease. The "therapeutically effective amount" will vary depending on the compound, the disease and its severity and the age, weight, etc., of the patient to be treated.

The present invention relates also to a process for the preparation of solid, preferably crystalline, forms of the compound of formula I, its hydrates or solvates, its salts and hydrates or solvates of its salts. The precise conditions under which crystals are formed may now be empirically determined and a number of methods are suitable in practice, including the crystallization conditions as described in Examples 3 to 17.

Crystallization-inducing conditions normally involve the use of an appropriate crystallization-inducing solvent, such as t-butylmethylether (TBME), methanol, ethanol, isopropanol or water or mixtures thereof. Conveniently, the amorphous compound is dissolved in the solvent at a temperature of normally at least 10° C. The solution may be produced by dissolving in a solvent any one or more of amorphous forms of the compound, and solvates thereof, such as hydrates, methanolates, ethanolates, isopropanolates, or formiates. Crystals may then be formed by conversion from solution, crystallization taking place at a temperature of between about 0° C. and the boiling point of the solvent. The dissolution and crystallization may be carried out in various conventional ways. For instance, amorphous compound may be dissolved in a solvent or a mixture of solvents in which it is readily soluble at elevated temperatures but in which it is only sparingly soluble at lower temperatures. Dissolution at elevated temperature is followed by cooling during which the desired crystals crystallize out of solution. A cooling and reheating step may be carried out several times, e.g. at least once, at least twice, at least 3×, at least 5×. The cooling and reheating temperatures are e.g. at least 5° C., at least 10° C. or at least 15° C. The low temperature of the cooling/heating cycles may e.g. be less than 15° C., less than 10° C., less than 5° C. or less than 0° C., whereas the high temperature may e.g. be at least 15° C., at least 20° C., at least 25° C. or at least 30° C.

Mixed solvents comprising a good solvent in which the compound is readily soluble, preferably, in amounts of at least 1% by weight at 30° C., and a poor solvent in which it is more sparingly soluble, preferably in amounts of not more than about 0.01% by weight at 30° C., may also be employed provided that crystallization from the mixture at a reduced temperature, of normally at least about, 0° C., is possible using the selected solvent mixture.

Alternatively, the difference in solubility of the crystals in different solvents may be used. For example, the amorphous compound may be dissolved in a good solvent in which it is highly soluble such as one in which it is soluble in amounts of at least 1% by weight at about 30° C. and the solution subsequently mixed with a poor solvent in which it is more sparingly soluble, such as one in which it is soluble in amounts of not more than about 0.01% by weight at about 30° C. Thus, the solution of the compound in the good solvent may be added to the poor solvent, while maintaining normally a temperature in excess of about 0° C., or the poor solvent may be added to the solution of the compound in the good solvent, again while normally maintaining a temperature in excess of about 0° C. Examples of good solvents may include lower alcohols, such as methanol, ethanol and isopropanol, formic acid acetic acid or acetone. An example of a poor solvent is e.g. water. Preferably, crystallization is effected at a temperature in the range of about 0° C. to about 40° C.

In an alternative embodiment of the process of the invention, solid amorphous compound is suspended at a temperature of normally at least about 0° C. in a solvent in which it is incompletely soluble, preferably only sparingly soluble, at that temperature. A suspension results in which particles of solid are dispersed, and remain incompletely dissolved in the solvent. Preferably the solids are maintained in a state of suspension by agitation e.g. by shaking or stirring. The suspension is kept at a temperature of normally about 0° C. or higher in order to effect a transformation of the starting solids into crystals. The amorphous solid compound suspended in a suitable solvent may be a solvate, e.g. hydrate, methanolate, ethanolate, acetate or formiate. The amorphous powder may be derived by drying a solvate.

It is preferred to add "seeds" of crystalline material to the solution in order to induce crystallization.

In accordance with a preferred embodiment of the present invention, the crystalline forms of formula I, its hydrates or solvates, its salts and hydrates or solvates of its salts have a high crystallinity. A crystal form is defined herein as having a "high crystallinity" or being "crystallographically pure" when it contains at most about 0.5% (w/w), e.g. at most about 0.1% (w/w) of other form. Thus e.g. "crystallographically pure Form AA" contains about 0.5% (w/w) or less, e.g. about 0.1% (w/w) or less of Form BB and/or another crystalline form. With respect to the content of amorphous form a "crystallographically pure" form contains less than about 5% of amorphous form or an amount below the limit of detection (i.e. no detactable amount) of amorphous form.

The following Examples illustrate the invention without limiting the scope thereof. Temperatures are given in degrees Celsius (° C.).

EXAMPLES

Example 1

2-Methyl-2-[4-(3-methyl-2-oxo-8-quinolin-3-yl-2,3-dihydro-imidazo[4,5-c]quinolin-1-yl)-phenyl]-propionitrile

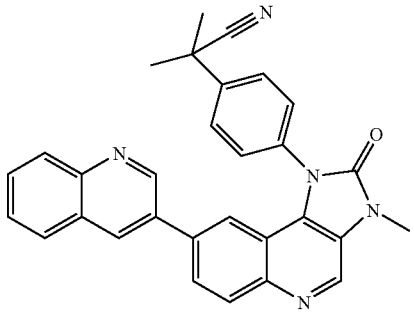 [SMILES: Cn1c(=O)n(-c2ccc(C(C)(C)C#N)cc2)c2c3cc(-c4cnc5ccccc5c4)ccc3ncc21]

In a suitable lab glass reactor are placed 45.0 g of starting 2[4-(8-bromo-3-methyl-2-oxo-2,3-dihydro-imidazo[4,5-c]quinolin-1-yl)-phenyl]2-methyl-propionitrile together with 2.25 g of bistriphenylphosphine palladium dichloride in 445 ml N,N-dimethylformamide. This mixture is heated to 95° C. and then a solution of 22.2 g of 3-quinoline boronic acid in a mixture of 225 ml DMF, 300 ml H$_2$O and 60 g of KHCO$_3$ is added. This mixture is heated for 2 h at 95° C. Then 1080 ml H₂O are added. The product 2-methyl-2-[4-(3-methyl-2-oxo-8-quinolin-3-yl-2,3-dihydro-imidazo[4,5-c]quinolin-1-yl)-phenyl]propionitrile precipitates. The mixture is cooled within 1.5 h to 0-5° C. After stirring at that temperature for 2 h the crude product is filtered and washed with 300 ml H₂O. This product is dried in vacuo at 60° C. for 18 h, to yield crude product.

40 g of this crude product is dissolved in 200 ml formic acid at 60° C. 8 g of active charcoal and Smopex 234 are added. The mixture is stirred at 60° C. for 1 h, the charcoal is filtered, the residue washed with 80 ml formic acid and then 175 ml formic acid are distilled off in vacuo. Then 320 ml methanol are added and the mixture is heated at reflux for 3 h. The purified product precipitates from the reaction mixture. The mixture is cooled to 0-5° C. within 1 h, then stirred 2 h at that temperature is finally filtered and washed with 80 ml cold methanol. This recrystallisation procedure is repeated again. Finally the twice recrystallised material is dried in vacuo at 60° C. to yield purified 2-Methyl-2-[4-(3-methyl-2-oxo-8-quinolin-3-yl-2,3-dihydro-imidazo[4,5-c]quinolin-1-yl)-phenyl]propionitrile.

Example 1a

5-Bromo-2-(2-nitro-vinylamino)-benzoic acid

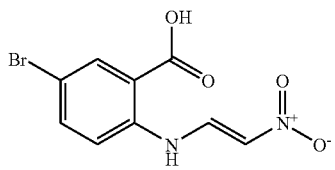 [SMILES: O=C(O)c1cc(Br)ccc1N/C=C/[N+](=O)[O-]]

A suspension of 25 g (16 mmol) of 2-amino-5-bromo-benzoic acid (Fluka, Buchs, Switzerland) in H₂O—HCl (37%) (10:1) is stirred for 8 h and then filtered (solution A). 8.17 g (255 mmol) of nitromethane (Fluka, Buchs, Switzerland) are added over 10 min to an ice-bath cooled mixture of 35 g of ice and 15.3 g (382 mmol) of NaOH. After stirring for 1 h at 0° C. and 1 h at rt, the solution is added at 0° C. to 28 g of ice and 42 ml of HCl (37%) (solution B). Solutions A and B are combined and the reaction mixture is stirred for 18 h at rt. The yellow precipitate is filtered off, washed with H₂O and dried in vacuo at 40° C. to give the title compound. ES-MS: 287, 289 (M+H)⁺, Br pattern; ¹H NMR (DMSO-d₆): δ 13.7-14.6/br s (1H), 12.94/d (1H), 8.07/d (1H), 8.03/dd (1H), 7.83/dd (1H), 7.71/d (1H), 6.76/d (1H).

Example 1b

6-Bromo-3-nitro-quinolin-4-ol

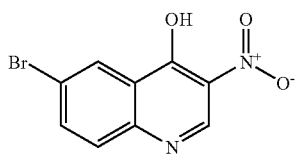 [SMILES: O=[N+]([O-])c1cnc2ccc(Br)cc2c1O]

29 g (101 mmol) of 5-bromo-2-(2-nitro-vinylamino)-benzoic acid (Example 1a) and 11.9 g (121 mmol) of potassium acetate in 129 ml (152 mmol) of acetic anhydride are stirred for 1.5 h at 120° C. The precipitate is filtered off and washed with acetic acid until the filtrate is colorless, then is washed with H₂O and dried in vacuo to give the title compound. ES-MS: 269, 271 (M+H)⁺, Br pattern; analytical HPLC: $t_{ret}$=2.70 min (Grad 1).

Example 1c

6-Bromo-4-chloro-3-nitro-quinoline

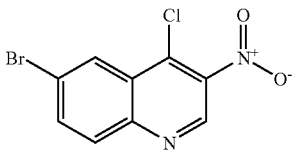 [SMILES: O=[N+]([O-])c1cnc2ccc(Br)cc2c1Cl]

20 g (74.3 mmol) of 6-bromo-3-nitro-quinolin-4-ol (Example 1b) in 150 ml (1.63 mol) of POCl₃ are stirred for 45 min at 120° C. The mixture is cooled to rt and poured slowly into ice-water. The precipitate is filtered off, washed with ice-cold water, and dissolved in CH₂Cl₂. The organic phase is washed with cold brine, and the aqueous phase is discarded. After drying over MgSO₄, the organic solvent is evaporated to dryness to provide the title compound. ¹H NMR (CDCl₃): δ 9.20/s (1H), 8.54/d (1H), 8.04/d (1H), 7.96/dd (1H); analytical HPLC: $t_{ret}$=4.32 min (Grad 1).

Example 1d

2-Methyl-2-(4-nitro-phenyl)-propionitrile

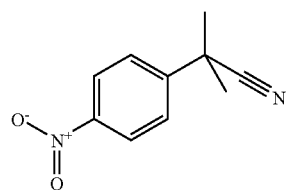

To 15 g (92.5 mmol) of (4-nitro-phenyl)-acetonitrile (Fluka, Buchs, Switzerland), 1.64 mg (5.09 mmol) of tetrabutylammonium bromide (Fluka, Buchs, Switzerland) and 43.3 g (305 mmol) of iodomethane in 125 mL of CH₂Cl₂ are added 10 g (250 mmol) of NaOH in 125 ml of water. The reaction mixture is stirred for 20 h at RT. After this time, the organic layer is separated, dried over MgSO₄, and evaporated to dryness. The residue is dissolved in diethylether and treated with black charcoal for 30 min, filtered over Celite and evaporated in vacuo to give the title compound as a pale yellow solid. Analytical HPLC: $t_{ret}$=3.60 minutes (Grad 1).

Example 1e (2-(4-Amino-phenyl)-2-methyl-propionitrile

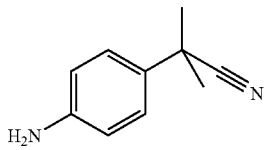

16 g (84.1 mmol) of 2-methyl-2-(4-nitro-phenyl)-propionitrile (Example 1d) and 4.16 g of Raney-Ni are shacked in 160 ml of THF-MeOH (1:1) under 1.1 bar of H$_2$ for 12 h at rt. After completion of the reaction, the catalyst is filtered-off and the filtrate is evaporated to dryness. The residue is purified by flash chromatography on silica gel (hexane-EtOAc 3:1 to 1:2) to provide the title compound as an oil. ES-MS: 161 (M+H)$^+$; analytical HPLC: t$_{ret}$=2.13 minutes (Grad 1).

Example 1f

2-[4-(6-Bromo-3-nitro-quinolin-4-ylamino)-phenyl]-2-methyl-propionitrile

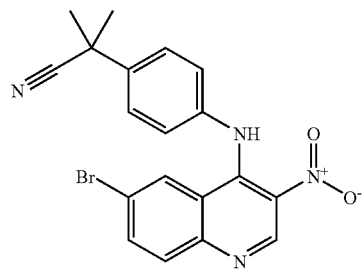 [SMILES: CC(C)(C#N)c1ccc(Nc2c([N+](=O)[O-])cnc3ccc(Br)cc23)cc1]

18 g (62.6 mmol) of 6-bromo-4-chloro-3-nitro-quinoline (Example 1c) and 11 g (68.9 mmol) of (2-(4-amino-phenyl)-2-methyl-propionitrile (Example 1e) are dissolved in 350 ml of acetic acid and stirred for 2 h. After this time, water is added and the yellow precipitate is filtered off and washed with H$_2$O. The solid is dissolved in EtOAc-THF (1:1), washed with sat. aqueous NaHCO$_3$ and dried over MgSO$_4$. The organic phase is evaporated to dryness to give the title compound as a yellow solid. ES-MS: 411, 413 (M+H)$^+$, Br pattern; analytical HPLC: t$_{ret}$=3.69 min (Grad 1).

Example 1g

2-[4-(3-Amino-6-bromo-quinolin-4-ylamino)-phenyl]-2-methyl-propionitrile

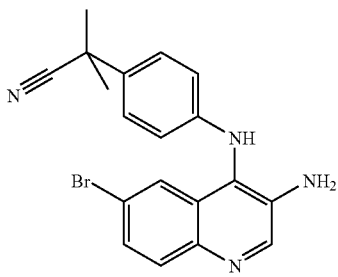 [SMILES: CC(C)(C#N)c1ccc(Nc2c(N)cnc3ccc(Br)cc23)cc1]

24 g (58.4 mmol) of 2-[4-(6-bromo-3-nitro-quinolin-4-ylamino)-phenyl]-2-methyl-propionitrile (Example 1e) is shacked in 300 ml of MeOH-THF (1:1) under 1.1 bar of H$_2$ in the presence of 8.35 g of Raney-Ni for 1 h. After completion of the reaction, the catalyst is filtered off and the filtrate is evaporated to dryness to give the title compound as a yellow foam. ES-MS: 381, 383 (M+H)$^+$, Br pattern; analytical HPLC: t$_{ret}$=3.21 min (Grad 1).

Example 1h

2-[4-(8-Bromo-2-oxo-2,3-dihydro-imidazo[4,5-c]quinolin-1-yl)-phenyl]-2-methyl-propionitrile

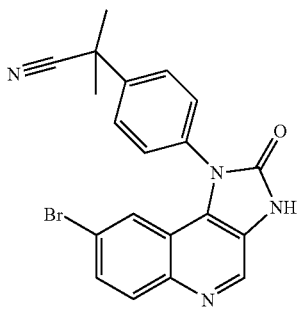 [SMILES: CC(C)(C#N)c1ccc(-n2c(=O)[nH]c3cnc4ccc(Br)cc4c32)cc1]

A solution of 5 g (13.1 mmol) of 2-[4-(3-amino-6-bromo-quinolin-4-ylamino)-phenyl]-2-methyl-propionitrile (Example 1g) and 1.59 g (15.7 mmol) of triethylamine in 120 ml CH$_2$Cl$_2$ is added over 40 min to a solution of 2.85 g (14.4 mmol) of trichloromethyl chloroformate (Fluka, Buchs, Switzerland) in 80 ml of CH$_2$Cl$_2$ at 0° C. with an ice-bath. The reaction mixture is stirred for 20 min at this temperature then is quenched with sat. aqueous NaHCO$_3$, stirred for 5 min and extracted with CH$_2$Cl$_2$. The organic layer is dried over Na$_2$SO$_4$, filtered and evaporated in vacuo to give crude title compound as a brownish solid. ES-MS: 407, 409 (M+H)$^+$, Br pattern; analytical HPLC: t$_{ret}$=3.05 min (Grad 1).

Example 1i

2-[4-(8-Bromo-3-methyl-2-oxo-2,3-dihydro-imidazo[4,5-c]quinolin-1-yl)-phenyl]-2-methyl-propionitrile

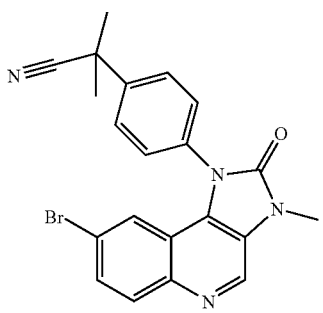 [SMILES: Cn1c(=O)n(-c2ccc(C(C)(C)C#N)cc2)c2c3cc(Br)ccc3ncc21]

To a solution of 3.45 g (8.47 mmol) of 2-[4-(8-bromo-2-oxo-2,3-dihydro-imidazo[4,5-c]quinolin-1-yl)-phenyl]-2-methyl-propionitrile (Example 1h), 1.8 g (12.7 mmol) of iodomethane (Fluka, Buchs, Switzerland) and 273 mg (0.847 mmol) of tetrabutylammonium bromide (Fluka, Buchs, Switzerland) in 170 ml of CH$_2$Cl$_2$ is added a solution of 508 mg (12.7 mmol) of NaOH (Fluka, Buchs, Switzerland) in 85 ml of $H_2O$. The reaction mixture is stirred for 2 days and 900 mg (6.35 mmol) of iodomethane and 254 mg (6.35 mmol) of NaOH in 5 ml of $H_2O$ are added. The reaction mixture is stirred for 1 day at rt After this time, the reaction is quenched with $H_2O$ and extracted with $CH_2Cl_2$ (2×). The organic layer is washed with brine, dried over $Na_2SO_4$, filtered and evaporated in vacuo to give the title compound as a beige solid. ES-MS: 421, 423 $(M+H)^+$, Br pattern; analytical HPLC: $t_{ret}$=3.15 min (Grad 1).

Example 2

2-Methyl-2-[4-(3-methyl-2-oxo-8-quinolin-3-yl-2,3-dihydro-imidazo[4,5-c]quinolin-1-yl)-phenyl]propionitrile p-toluenesulfonate salt 26.5 g of 2-Methyl-2-[4-(3-methyl-2-oxo-8-quinolin-3-yl-2,3-dihydro-imidazo[4,5-c]quinolin-1-yl)-phenyl]propionitrile are placed together with 55 ml formic acid into a glass reactor. This mixture is heated to 60° C. to get a clear solution. This solution is clear filtered and washed with 36 ml formic acid. Then formic acid is distilled off until the volume of the residual solution is 55 ml. Then a solution of 11.3 g of p-toluenesulfonic acid in 228 ml acetone is added at 50° C., followed by further addition of 822 ml acetone within 30 minutes. The salt precipitates from the reaction mixture. The mixture is cooled to 0° C. within 2 h, stirred at that temperature for 3 h, is then filtered and washed with 84 ml acetone. The product is dried at 60° C. in vacuo for 18 h to yield 29.8 g (82.4%) of the 2-Methyl-2-[4-(3-methyl-2-oxo-8-quinolin-3-yl-2,3-dihydro-imidazo[4,5-c]quinolin-1-yl)-phenyl]propionitrile p-toluenesulfonate salt (crystalline form A).

The crystalline forms of the present invention are synthesized in accordance with the following examples which are illustrative without limiting the scope of the present invention.

Example 3

Preparation of form A of 2-methyl-2-[4-(3-methyl-2-oxo-8-quinolin-3-yl-2,3-dihydro-imidazo[4,5-c]quinolin-1-yl)-phenyl]-propionitrile Form A of compound I can be manufactured in the following way: 241 g of free base are dissolved 2.4 l acetic acid at 50° C. The solution is clear filtered, washed with 250 ml acetic acid and then at 50° C. 7.2 l of water are added. The free base starts precipitating. The mixture is cooled within 1 h to 25° C., is then filtered and washed with 10 l $H_2O$. The free base is then dried in vacuo at 50° C. over night to yield 204 g of free base.

Example 4

Preparation of form B of 2-methyl-2-[4-(3-methyl-2-oxo-8-quinolin-3-yl-2,3-dihydro-imidazo[4,5-c]quinolin-1-yl)-phenyl]-propionitrile 0.47 g of free base (compound I) are placed into a reactor together with 2 ml of formic acid. The mixture is heated to 60° C. to get a clear solution. Then 5.2 ml of methanol are added. The mixture is heated at 65° C. for 2 h. Compound I starts to precipitate (the formic acid is esterified to the corresponding methylester under these conditions). The mixture is cooled to room temperature and is stirred at room temperature for further 2 hours. Then the precipitate is filtered, washed with 2 ml methanol and dried in vacuo at 60° C. for 17 h to yield form B of compound I.

Example 5

Preparation of form C of 2-methyl-2-[4-(3-methyl-2-oxo-8-quinolin-3-yl-2,3-dihydro-imidazo[4,5-c]quinolin-1-yl)-phenyl]-propionitrile Compound I changes its polymorphic form after equilibration in different solvents (slurry experiment with approx. 20 mg sample and 0.5 ml solvent at 25° C. for 24 hours equilibration time (with agitation)). In methanol, methanol/water, DMF, ethanol, ethylacetate and THF the new form C can be observed.

Compound I (0.94 g) is added to 14 ml ethanol and heated to 62° C. Then 3 ml of formic acid are added to get a clear solution. The mixture is stirred 2 h at 62° C., whereby the free base starts precipitating. The mixture is cooled to room temperature, is stirred at room temperature for 2.5 hours and is then filtered off. The filter cake is then washed with 5 ml ice cold ethanol and then dried in vacuo at 60° C. over night, to obtain form C of compound I.

Alternatively compound I is dissolved in formic acid at 60° C., clear filtered and then methanol is added. After stirring for 2 hours at 65° C., the mixture is cooled to room temperature, the salt is filtered and washed with ice cold methanol to yield form C of compound I.

Example 6

Preparation of form D of 2-methyl-2-[4-(3-methyl-2-oxo-8-quinolin-3-yl-2,3-dihydro-imidazo[4,5-c]quinolin-1-yl)-phenyl]-propionitrile Compound I changes its polymorphic form after equilibration in different solvents (slurry experiment with approx. 20 mg sample and 0.5 ml solvent at 25° C. for 24 hours equilibration time (with agitation)). In isopropanol as solvent the new form D can be observed.

Example 7

Preparation of form $H_4$ of 2-methyl-2-[4-(3-methyl-2-oxo-8-quinolin-3-yl-2,3-dihydro-imidazo[4,5-c]quinolin-1-yl)-phenyl]-propionitrile monohydrate This compound is obtained after crystallization by slow solvent evaporation from DMF solution at room temperature.

Example 8

Preparation of form A of 2-methyl-2-[4-(3-methyl-2-oxo-8-quinolin-3-yl-2,3-dihydro-imidazo[4,5-c]quinolin-1-yl)-phenyl]-propionitrile monotosylate 2-methyl-2-[4-(3-methyl-2-oxo-8-quinolin-3-yl-2,3-dihydro-imidazo[4,5-c]quinolin-1-yl)-phenyl]-propionitrile (compound of formula I) is dissolved in formic acid at 56° C. and the resulting solution is clear filtered. The filtrate is then concentrated and a solution of p-toluenesulfonic acid (1.05 eq) in acetone is added within 30 minutes. After 25% and 50% of the addition volume, the mixture is seeded to initiate crystallization. A further amount of acetone is added and the suspension is cooled down to 0° C. The crystallized product (form A of compound I monotosylate) is collected by centrifugation and dried at 60° C. under vacuum.

Example 9

Preparation of form B of 2-methyl-2-[4-(3-methyl-2-oxo-8-quinolin-3-yl-2,3-dihydro-imidazo[4,5-c]quinolin-1-yl)-phenyl]-propionitrile monotosylate A phase transformation of form A prepared according to Example 8 to another crystalline form, further on named form B, can be observed at temperatures above 70° C. (this can also be detected in the corresponding DSC. The transformation is reversible as found by DSC experiments. Form A and Form B have an enantiotropic relationship.

Example 10

Preparation of form $H_A$ of 2-methyl-2-[4-(3-methyl-2-oxo-8-quinolin-3-yl-2,3-dihydro-imidazo[4,5-c]quinolin-1-yl)-phenyl]-propionitrile monotosylate monohydrate A saturated solution of compound I ditosylate in ethanol/acetone (1:1) can be used in a slow solvent evaporation experiment at 25° C. The formation of single crystals of compound 1 monotosylate monohydrate (form $H_A$) has been observed and the single crystal structure could be calculated.

Example 11

Preparation of form $H_B$ of 2-methyl-2-[4-(3-methyl-2-oxo-8-quinolin-3-yl-2,3-dihydro-imidazo[4,5-c]quinolin-1-yl)-phenyl]-propionitrile monotosylate dihydrate By equilibration experiment of compound I ditosylate in water (after 3 days time) at 25° C. the formation of single crystals was observed. The crystal structure could be determined and was calculated to be compound I monotosylate dihydrate (form $H_B$).

Example 12

Preparation of form $S_A$ of 2-methyl-2-[4-(3-methyl-2-oxo-8-quinolin-3-yl-2,3-dihydro-imidazo[4,5-c]quinolin-1-yl)-phenyl]-propionitrile monotosylate diformic acid solvate The single crystal structure of compound I monotosylate diformic acid solvate was determined by X-ray diffraction (modification $S_A$). Suitable single crystals were obtained by equilibration of compound I monotosylate in acetone/formic acid (1:1 (v/v)) solvent mixture at 50° C. after cooling down to room temperature. The stoichiometry of this salt could be determined to be 1:1.7 (compound I p-toluenesulfonate salt/formic acid). The stoichiometry has been calculated to be 1:1.7 but as one solvate molecule is disordered it seems to be that a stoichiometry of 1:2 is probable. Due to the possibility for formic acid to leave the structure stoichiometric ratios below 1:2 are observed.

Example 13

Preparation of form A of 2-methyl-2-[4-(3-methyl-2-oxo-8-quinolin-3-yl-2,3-dihydro-imidazo[4,5-c]quinolin-1-yl)-phenyl]-propionitrile ditosylate When a solution of compound I in formic acid is treated with an acetone solution of p-toluene sulfonic acid (1.25 eq) the ditosylate salt of compound I can be isolated as a second crop from crystallization from the mother liquor after filtering off the monotosylate salt.

The compound I ditosylate salt has initial loss on drying of 0.4% (up to 140° C.). DSC data showed a melting at approx. 262° C. with a melting enthalpy of approx. 93 J/g.

Example 14

Preparation of form $H_A$ of 2-methyl-2-[4-(3-methyl-2-oxo-8-quinolin-3-yl-2,3-dihydro-imidazo[4,5-c]quinolin-1-yl)-phenyl]-propionitrile ditosylate trihydrate From a saturated solution of compound I ditosylate salt in dichlormethane/methanol (1:1 (v/v)) mixture the compound I ditosylate trihydrate form (modification $H_A$) could be observed and single crystals were found.

Example 15

Preparation of amorphous 2-methyl-2-[4-(3-methyl-2-oxo-8-quinolin-3-yl-2,3-dihydro-imidazo[4,5-c]quinolin-1-yl)-phenyl]-propionitrile monotosylate Amorphous material has been produced by spray drying of compound I monotosylate. The glass transition, Tg, has been observed by DSC at approx. 128° C. After recrystallization at approx. 175° C. the substance melted at approx. 279° C. with an melting enthalpy of approx. 65 J/g.

Example 16

Preparation of form $S_C$ of 2-methyl-2-[4-(3-methyl-2-oxo-8-quinolin-3-yl-2,3-dihydro-imidazo[4,5-c]quinolin-1-yl)-phenyl]-propionitrile monotosylate diformic acid solvate monohydrate The single crystal structure of compound I monotosylate diformic acid solvate monohydrate was determined by X-ray diffraction (modification $S_C$). Suitable single crystals were obtained by equilibration of compound I monotosylate in methylisobutylketone/formic acid (1:1 (v/v)) solvent mixture at 50° C. after cooling down to room temperature.

Example 17

Preparation of form $S_B$ of 2-methyl-2-[4-(3-methyl-2-oxo-8-quinolin-3-yl-2,3-dihydro-imidazo[4,5-c]quinolin-1-yl)-phenyl]-propionitrile monotosylate diacetic acid solvate The single crystal structure of compound I monotosylate diacetic acid solvate was determined by X-ray diffraction (modification $S_C$). Suitable single crystals were obtained by equilibration of compound I monotosylate in methylisobutylketone/acetic acid (1:1 (v/v)) solvent mixture at 50° C. after cooling down to room temperature.

What is claimed is:
1. A crystalline form of the compound of formula I

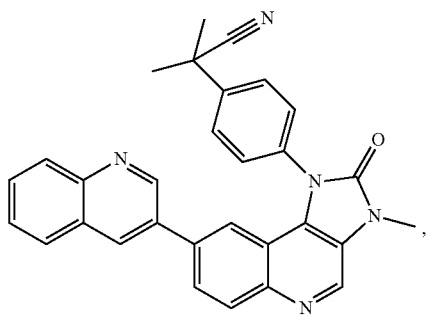

or of a hydrate of the compound of formula I, or of a monotosylate or ditosylate salt of the compound of formula I, or of a hydrate or solvate of a monotosylate salt of the compound of formula I, or of a hydrate of a ditosylate salt of the compound of formula I, wherein the crystalline form is selected from the group consisting of crystalline form A of the compound of formula I, crystalline form B of the compound of formula I, crystalline form C of the compound of formula I, crystalline form D of the compound of formula I, crystalline form $H_A$ of the monohydrate of compound I, crystalline form A of the monotosylate salt of the compound of formula I, crystalline form B of the monotosylate salt of the compound of formula I, crystalline form $H_A$ of the monohydrate of the monotosylate salt of the compound of formula I, crystalline form $H_B$ of the dihydrate of the monotosylate salt of compound of formula I, crystalline form $S_A$ of the diformic acid solvate of the monotosylate salt of compound I, crystalline form A of the ditosylate salt of the compound of formula I, crystalline form $H_A$ of the trihydrate of the ditosylate salt of the compound of formula I, crystalline form $S_C$ of the monohydrate of the diformic acid solvate of the monotosylate salt of the compound of formula I, and crystalline form $S_B$ of the diacetic acid solvate of the monotosylate salt of the compound of formula I.

2. Compound of formula I according to claim 1 in crystalline form A.

3. A compound according to claim 2 which shows on X-ray diffraction a peak at an angle of diffraction 2Theta of 8.4°+/−0.3°.

4. Compound of formula I according to claim 1 in crystalline form B.

5. A compound according to claim 3 which shows on X-ray diffraction a peak at an angle of diffraction 2Theta of 6.9°+/−0.3°.

6. Compound of formula I according to claim 1 in crystalline form C.

7. A compound according to claim 6 which shows on X-ray diffraction a peak at an angle of diffraction 2Theta of 14.7°+/−0.3°.

8. Compound of formula I according to claim 1 in crystalline form D.

9. A compound according to claim 8 which shows on X-ray diffraction a peak at an angle of diffraction 2Theta of 23.9°+/−0.3°.

10. A monohydrate of compound of formula I according to claim 1 in crystalline form $H_A$.

11. A compound according to claim 10 which shows on X-ray diffraction a peak at an angle of diffraction 2Theta of 17.6°+/−0.3°.

12. A monotosylate salt of compound of formula I according to claim 1 in crystalline form A.

13. A compound according to claim 12 which shows on X-ray diffraction a peak at an angle of diffraction 2Theta of 5.7°+/−0.3°.

14. A compound according to claim 12 which shows on X-ray diffraction peaks at an angle of diffraction 2Theta of 5.4°+/−0.3°; 5.7°+/−0.3° and 17.2°+/−0.3°.

15. A compound according to claim 12 which shows an X-ray diffraction diagram essentially as outlined in FIG. 6.

16. A monotosylate salt of compound of formula I according to claim 1 in crystalline form B.

17. A compound according to claim 16 which shows on X-ray diffraction a peak at an angle of diffraction 2Theta of 5.8°+/−0.3°.

18. A compound according to claim 16 which shows on X-ray diffraction peaks at an angle of diffraction 2Theta of 5.8°+/−0.3°; 17.8°+/−0.3° and 18.7°+/−0.3°.

19. A monohydrate of the monotosylate salt of compound of formula I according to claim 1 in crystalline form $H_A$.

20. A compound according to claim 19 which shows on X-ray diffraction a peak at an angle of diffraction 2Theta of 6.5°+/−0.3°.

21. A dihydrate of the monotosylate salt of compound of formula I according to claim 1 in crystalline form $H_B$.

22. A compound according to claim 21 which shows on X-ray diffraction a peak at an angle of diffraction 2Theta of 6.9°+/−0.3°.

23. A diformic acid solvate of the monotosylate salt of compound of formula I according to claim 1 in crystalline form $S_A$.

24. A compound according to claim 23 which shows on X-ray diffraction a peak at an angle of diffraction 2Theta of 5.8°+/−0.3°.

25. A ditosylate salt of compound of formula I according to claim 1 in crystalline form A.

26. A compound according to claim 25 which shows on X-ray diffraction a peak at an angle of diffraction 2Theta of 22.4°+/−0.3°.

27. A trihydrate of the ditosylate salt of compound of formula I according to claim 1 in crystalline form $H_A$.

28. A compound according to claim 27 which shows on X-ray diffraction a peak at an angle of diffraction 2Theta of 4.7°+/−0.3°.

29. A monohydrate of the diformic acid solvate of the monotosylate salt of compound of formula I according to claim 1 in crystalline form $S_C$.

30. A compound according to claim 29 which shows on X-ray diffraction a peak at an angle of diffraction 2Theta of 5.6°+/−0.3°.

31. A diacetic acid solvate of the monotosylate salt of compound of formula I according to claim 1 in crystalline form $S_B$.

32. A compound according to claim 31 which shows on X-ray diffraction a peak at an angle of diffraction 2Theta of 5.7°+/−0.3°.

* * * * *